(12) United States Patent
Bahn et al.

(10) Patent No.: US 10,197,580 B2
(45) Date of Patent: Feb. 5, 2019

(54) BIOMARKERS ASSOCIATED WITH SCHIZOPHRENIA

(71) Applicant: Cambridge Enterprise Limited, Cambridge, Cambridgeshire (GB)

(72) Inventors: Sabine Bahn, Cambridge (GB); Man Kuan Chan, Cambridge (GB)

(73) Assignee: Cambridge Enterprises Limited, Cambridge (GB)

( * ) Notice: Subject to any disclaimer, the term of this patent is extended or adjusted under 35 U.S.C. 154(b) by 0 days.

(21) Appl. No.: 15/125,069

(22) PCT Filed: Mar. 9, 2015

(86) PCT No.: PCT/GB2015/050674
§ 371 (c)(1),
(2) Date: Sep. 9, 2016

(87) PCT Pub. No.: WO2015/136251
PCT Pub. Date: Sep. 17, 2015

(65) Prior Publication Data
US 2017/0016921 A1     Jan. 19, 2017

(30) Foreign Application Priority Data
Mar. 10, 2014    (GB) .................................. 1404189.1

(51) Int. Cl.
*G01N 33/68*    (2006.01)

(52) U.S. Cl.
CPC ... *G01N 33/6896* (2013.01); *G01N 2333/475* (2013.01); *G01N 2333/4728* (2013.01); *G01N 2333/4745* (2013.01); *G01N 2333/545* (2013.01); *G01N 2333/5421* (2013.01); *G01N 2333/575* (2013.01); *G01N 2333/59* (2013.01); *G01N 2333/705* (2013.01); *G01N 2333/70539* (2013.01); *G01N 2333/775* (2013.01); *G01N 2333/78* (2013.01); *G01N 2333/805* (2013.01); *G01N 2333/916* (2013.01); *G01N 2333/9121* (2013.01); *G01N 2333/91205* (2013.01); *G01N 2333/948* (2013.01); *G01N 2333/96447* (2013.01); *G01N 2333/99* (2013.01); *G01N 2800/302* (2013.01); *G01N 2800/60* (2013.01)

(58) Field of Classification Search
CPC ....... G01N 33/6896; G01N 2333/4728; G01N 2333/4745; G01N 2333/475; G01N 2333/5421; G01N 2333/70539; G01N 2333/545; G01N 2333/575; G01N 2333/59; G01N 2333/705; G01N 2333/775; G01N 2333/78; G01N 2333/805; G01N 2333/91205; G01N 2333/9121; G01N 2333/916; G01N 2333/948; G01N 2333/96447; G01N 2333/99; G01N 2800/60
See application file for complete search history.

(56) References Cited

U.S. PATENT DOCUMENTS

| | | |
|---|---|---|
| 6,420,108 B2 | 7/2002 | Mack et al. |
| 2004/0053292 A1 | 3/2004 | Tschopp et al. |
| 2006/0099593 A1 | 5/2006 | Nawa et al. |
| 2008/0020475 A1 | 1/2008 | Mapes et al. |
| 2009/0175827 A1 | 7/2009 | Byrom et al. |
| 2011/0165554 A1 | 7/2011 | Levin et al. |
| 2014/0200151 A1 | 7/2014 | Bahn et al. |
| 2017/0016921 A1 | 1/2017 | Bahn et al. |

FOREIGN PATENT DOCUMENTS

| | | |
|---|---|---|
| EP | 15 710 233.6 | 9/2017 |
| EP | 15 710 233.6 | 5/2018 |
| WO | 2008/090319 | 7/2008 |
| WO | 2009/077763 | 6/2009 |
| WO | WO 2011/030153 A1 | 3/2011 |
| WO | WO 2012/085555 A2 | 6/2012 |
| WO | PCT/GB2011/052526 | 10/2012 |
| WO | WO 2015/136251 A1 | 9/2015 |

OTHER PUBLICATIONS

Yung et al. Mapping the onset of psychosis: the Comprehensive Assessment of At-Risk Mental States. Aust N Z J Psychiatry. Nov.-Dec. 2005;39(11-12):964-71.*
Chan et al., "Converging evidence of blood-based biomarkers for schizophrenia: an update", Int. Rev. Neurobiol., Biomark. Neurol. Psych. Dis., vol. 101, pp. 95-144 (2011).
Chan et al., "Applications of blood-based protein biomarker strategies in the study of psychiatric disorders", Progress Neurobiol., vol. 122, pp. 45-72 (2014).
Cox et al., "The potential of immune biomarkers to advance personalized medicine approaches for schizophrenia", J Nerv. Mental Dis., vol. 203, No. 5, pp. 393-399 (2015).
Domenici et al., "Plasma protein biomarkers for depression and schizophrenia by multi analyte profiling of case-control collections", PLoS One, vol. 5, Issue 2, No. e9166, pp. 1-12 (2010).
Guest et al., "The use of proteomic biomarkers for improved diagnosis and stratification of schizophrenia patients", Biomark. Med., vol. 8, No. 1, pp. 15-27 (2014).
International Search Report from International Application No. PCT/GB2015/050674 dated May 19, 2015, application now published as International Publication No. WO2015/136251, on Sep. 17, 2015.
Levin et al., "Global proteomic profiling reveals altered proteomic signature in schizophrenia serum", Mol. Psych., vol. 15, No. 11, pp. 1088-1100 (2010).
Schwarz et al., "Identification of a biological signature for schizophrenia in serum", Mol. Psych., vol. 17, No. 5, pp. 494-502 (2012).

(Continued)

*Primary Examiner* — Gregory S Emch
(74) *Attorney, Agent, or Firm* — Evan Law Group LLC

(57) ABSTRACT

The invention relates to biomarkers and methods of diagnosing or monitoring schizophrenia, or a predisposition thereto.

27 Claims, 8 Drawing Sheets

(56) References Cited

OTHER PUBLICATIONS

Schwarz et al., "Validation of a blood-based laboratory test to aid in the confirmation of a diagnosis of schizophrenia", Biomarker Insights, Libertas Academia, vol. 5, pp. 39-47 (2010).
Takayanagi et al., "Relationships between serum leptin level and severity of positive symptoms in schizophrenia", Neurosci. Res., vol. 77, pp. 97-101 (2013).
Yung, A.R. et al. "Mapping the onset of psychosis: the comprehensive assessment of at-risk mental states", Australian and New Zealand Journal of Psychiatry, vol. 39, pp. 964-971, (2005).
Bromet, E.J. et al., "Long-term diagnostic stability and outcome in recent first-episode cohort studies of schizophrenia", Schizophrenia Bulletin, vol. 31, No. 3, pp. 639-649, (2005).
Fusar-Poli, P. et al., "Predicting psychosis meta-analysis of transition outcomes in individuals at high clinical risk", Arch Gen Psychiatry, vol. 69, No. 3, pp. 220-229, (2012).
Fusar-Poli, P. et al., "Attenuated psychosis syndrome: Ready for DSM-5.1?", Annual Review of Clinical Psychology, vol. 10, pp. 155-192, (2014).
Van der Gaag, M. et al., "Preventing a first episode of psychosis: Meta-analysis of randomized controlled prevention trials of 12 month and longer-term follow-ups", Schizophrenia Reseach, vol. 149, pp. 56-62, (2013).
Tandon, R., "Definition of psychotic disorders in the DSM-5 too radical, too conservative, or just right!" Schizophrenia Research, vol. 150, pp. 1-2, (2013).
Owens, J., "Funding for accelerating drug development initiative critical", Nature Reviews Drug Discovery, vol. 5, No. 4, p. 271, (2006).
Goodsaid, F. et al., "Implementing the U.S. FDA guidance on pharmacogenomic data submissions", Environmental and Molecular Mutagenesis, vol. 48, No. 5, pp. 354-358, (2007).
Li, Y. et al., "Association between antibodies to multiple infectious and food antigens and new onset schizophrenia among US military personnel", Schizophrenia Research, vol. 151, No. 1-3, pp. 36-42, (2013).
Millikan, A.M. et al., "Evaluation of data obtained from military disability medical administrative databases for service members with schizophrenia or bipolar disorder", Miltary Medicine, vol. 172, No. 10, pp. 1032-1038, (2007).
Schwarz, E. et al., "Identification of a blood-based biological signature in subjects with psychiatric disorders prior to clinical manifestation", The World Journal of Biological Psychiatry, vol. 13, No. 8, pp. 627-632, (2012).
Magaud, E. et al., "Subjects at ultra high risk for psychosis have "heterogeneous" intellectual functioning profile: A multiple-case study", Schizophrenia Research, vol. 152, No. 2-3, pp. 415-420, (2014).
Magaud, E. et al., "Altered semantic but not phonological verbal fluency in young help-seeking individuals with ultra high risk of psychosis", Schizophrenia Research, vol. 123, pp. 53-58, (2010).
Bossuyt, P.M. et al. "Towards complete and accurate reporting of studies of diagnostic accuracy: the STARD initiative", Croatian Medical Journal, vol. 44, No. 5, pp. 635-638, (2003).
Johnson, W.E. et al., "Adjusting batch effects in microarray expression data using empirical bayes methods", Biostatistics, vol. 8, No. 1, pp. 118-127, (2006).
Tibshirani, R., "Regression shrinkage and selection via the lasso", Journal of the Royal Statistical Society, Series B (Methodological), vol. 58, No. 1, pp. 267-288, (1996).
Ruhrmann, S. et al., "Chances and risks of predicting psychosis", European Archives of Psychiatry and Clinical Neuroscience, vol. 262, supplement 2, pp. S85-S90, (2012).
Zarogianni, E. et al., "Towards the identification of imaging biomarkers in schizophrenia, using multivariate pattern classification at a single-subject level", NeuroImage: Clinical, vol. 3, pp. 279-289, (2013).
Schwarz, E. et al., "Identification of subgroups of schizophrenia patients with changes in either immune or growth factor and hormonal pathways", Schizophrenia Bulletin, vol. 40, No. 4, pp. 787-795, (2014).
Domenici, E. et al., "Plasma protein biomarkers for depression and schizophrenia by multi analyte profiling of case-control collections", PLoS One, vol. 5, No. 2, pp. 1-12, (2010).
Miller, B.J. et al., "Meta-analysis of cytokine alterations in schizophrenia: Clinical status and antipsychotic effects", Biological Psychiatry, vol. 70, pp. 663-671, (2011).
Takayanagi, Y. et al., "Relationships between serum leptin level and severity of positive symptoms in schizophrenia", Neuroscience Research, vol. 77, pp. 97-101, (2013).
Li, Y. et al., "Label-free quantitative proteomic analysis reveals dysfunction of complement pathway in peripheral blood of schizophrenia patients: evidence for the immune hypothesis of schizophrenia", Molecular BioSystems, vol. 8, pp. 2664-2671, (2012).
Muller, N. et al., "Anti-inflammatory treatment in schizophrenia", Progress in Neuro-Psychopharmacology & Biological Psychiatry, vol. 42, pp. 146-153, (2013).
Bahn, S. et al., "Challenges of introducing new biomarker products for neuropsychiatric disorders into the market", International Review of Neurobiology, Biomarkers of Neurological and Psychiatric Disease, vol. 101, pp. 299-327, (2011).
International Search Report and written opinion dated May 19, 2015 for PCT application No. PCT/GB2015/050674, 11 pages.
International Preliminary Report on Patentability dated Sep. 13, 2016 for PCT application No. PCT/GB2015/050674, 7 pages.
Schwarz, E. et al., "Validation of a blood-based laboratory test to aid in the confirmation of a diagnosis of schizophrenia", Biomarker Insights, vol. 5, pp. 39-47, (2010).
Bossuyt, P.M. et al., "Towards complete and accurate reporting of studies of diagnostic accuracy: The STARD Initiative", Clinical Chemistry, vol. 49, No. 1, pp. 1-6, (2003).
Benjamini, Y. et al., "Controlling the false discovery rate: A practical and powerful approach to multiple testing", Journal of the Royal Statistical Society, Series B (Methodological), vol. 57, No. 1, pp. 289-300, (1995).
Seaton, B.E. et al., "Sources of heterogeneity in schizophrenia: The role of neuropsychological functioning", Neuropsychology Review, vol. 11, No. 1, pp. 45-67, (2001).
Ferrier, I.N. et al., "Neuropsychological function in euthymic patients with bipolar disorder", British Journal of Psychiatry, vol. 175, pp. 246-251, (1999).
Raja, M. et al., "Asperger's disorder in the emergency psychiatric setting", General Hospital Psychiatry, vol. 23, No. 5, pp. 285-293, (2001).
Fleischhacker, W., "Negative symptoms in patients with schizophrenia with special reference to the primary versus secondary distinction", L'Encephale, Sp. 1, pp. 12-14, (2000).
Riecher-Rossler, A. et al., "Early detection and treatment of schizophrenia: how early?", Acta Psychiatrica Scandinavica, vol. 113, supplemental 429, pp. 73-80, (2006).
Blashki, G. et al, "Managing schizophrenia in general practice", Australian Family Physician, vol. 33, No. 4, pp. 221-227, (2004).
Ferguson, G.D. et al., "Synaptotagmin IV biochemistry, genetics, behavior, and possible links to human psychiatric disease", Molecular Neurobiology, vol. 23, issue 2/3, pp. 173-185, (2001).
Geddes, J. et al., "Atypical antipsychotics in the treatment of schizophrenia: systematic overview and meta-regression analysis", British Medical Journal, vol. 321, pp. 1371-1376. (2000).
Nnadi, C.U. et al., "Individualizing antipsychotic drug therapy in schizophrenia: The promise of pharmacogenetics", Current Psychiatry Reports, vol. 9, issue 4, pp. 313-318, (2007).
Pepe, G. et al., "Lipoprotein(a) in the cerebrospinal fluid of neurological patients with blood-cerebrospinal fluid barrier dysfunction", Clinical Chemistry, vol. 52, No. 11, pp. 2043-2048, (2006).
"Clinical chemistry reagents", Randox, 2 pages, found at web.archive.org/web/20080531145435/http://www.randox.com:80/English/products.cfm?ccs=686 (May 31, 2008), printed on Jun. 13, 2018.
Sudhof, T.C., "Synaptotagmins: Why so many?", The Journal of Biological Chemistry, vol. 277, No. 10, pp. 7629-7632, (2002).

(56) References Cited

OTHER PUBLICATIONS

Yokota, H. et al., "Polymorphic 33-bp repeats with promoter-like activity in synaptotagmin 11 gene", DNA Research, vol. 10, pp. 287-289, (2003).
Bock, E. "Immunoglobulins, prealbumin, transferrin, albumin, and alpha2-macroglobulin in cerebrospinal fluid and serum in schizophrenic patients", Birth Defects: Original Article Series, vol. 14, No. 5, pp. 283-295, (1978).
Wong, C-T. et al., "Acute phase proteins in male Chinese schizophrenic patients in Singapore", Schizophrenia Research, vol. 22, pp. 165-171, (1996).
International Search Report and written opinion dated Oct. 29, 2012 for PCT application No. PCT/GB2011/052526, 18 pages.
U.S. Appl. No. 13/995,848, dated Nov. 10, 2015, U.S.
U.S. Appl. No. 13/995,848, dated Feb. 25, 2016, U.S.
U.S. Appl. No. 13/995,848, dated Jun. 21, 2016, U.S.
U.S. Appl. No. 13/995,848, dated Aug. 29, 2016, U.S.
U.S. Appl. No. 13/995,848, dated Oct. 3, 2016, U.S.
U.S. Appl. No. 13/995,848, dated Apr. 27, 2017, U.S.
U.S. Appl. No. 13/995,848, dated Jul. 7, 2017, U.S.
U.S. Appl. No. 13/995,848, dated Sep. 28, 2017, U.S.
U.S. Appl. No. 13/995,848, dated Apr. 12, 2018, U.S.

\* cited by examiner

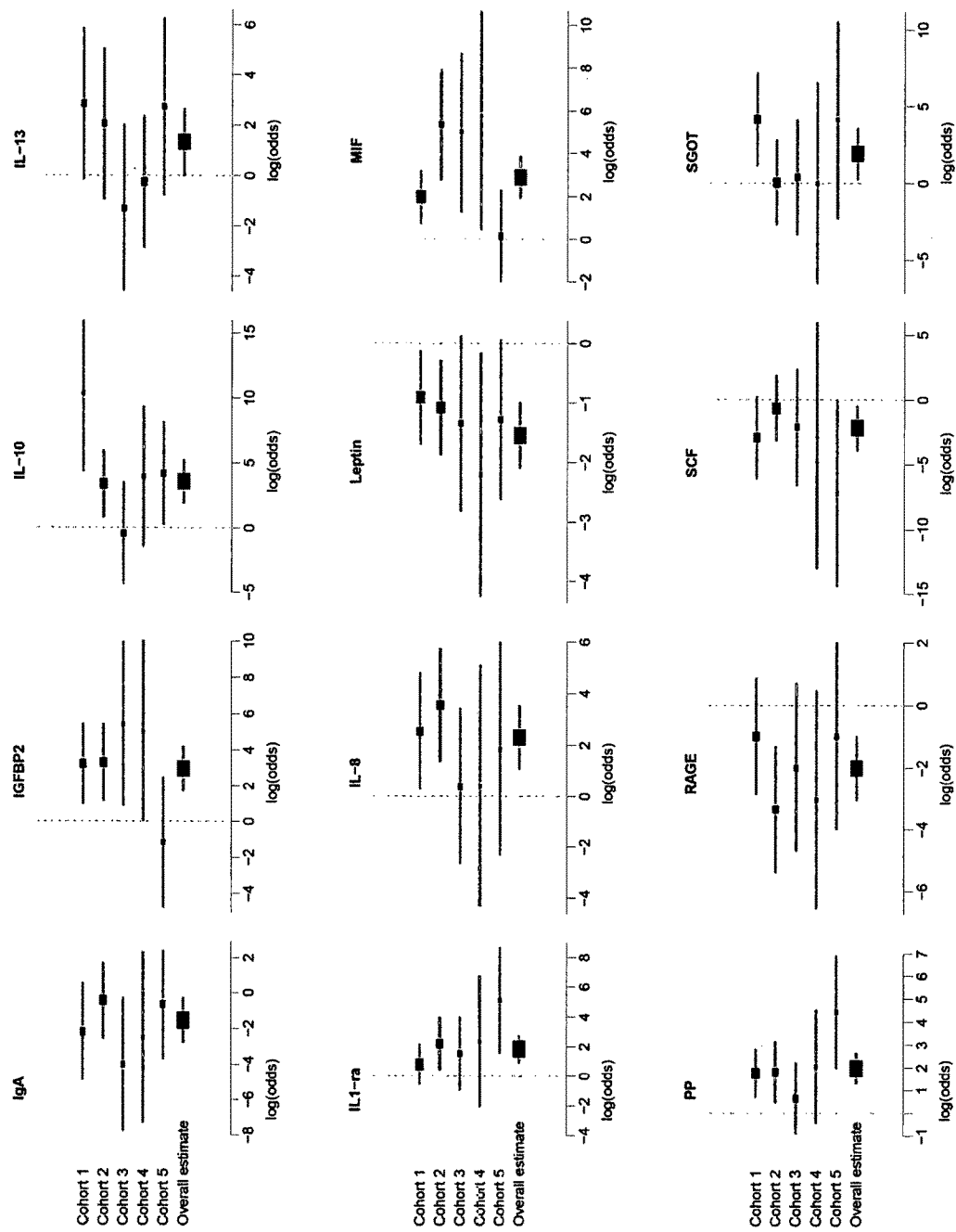
FIGURE 6 (CTD)

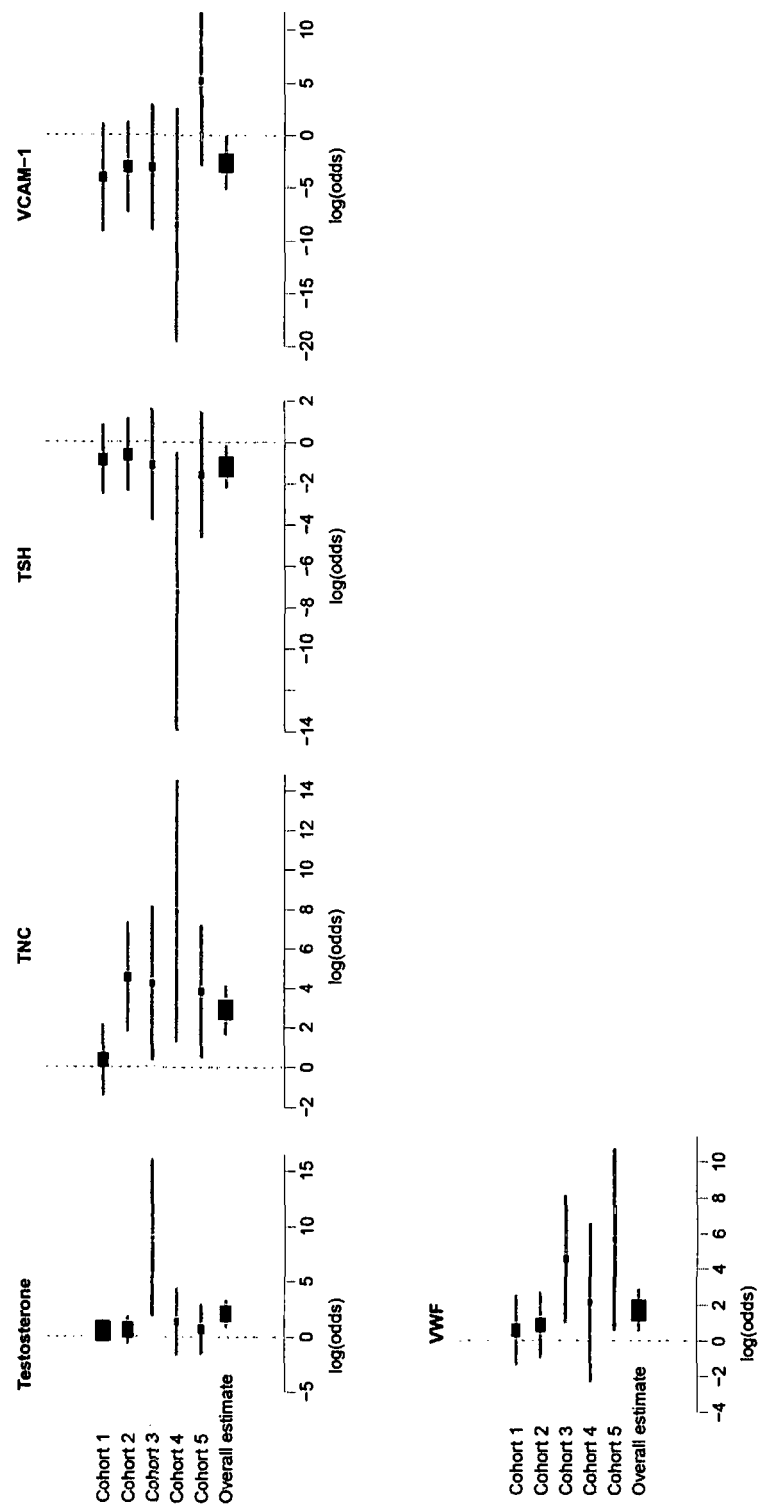
FIGURE 6 (CTD)

BIOMARKERS ASSOCIATED WITH SCHIZOPHRENIA

CROSS-REFERENCE TO RELATED APPLICATIONS

This application is a U.S. National Stage of International Patent Application No. PCT/GB2015/050674, filed Mar. 9, 2015, which claims the benefit of priority of GB Application No. 1404189.1, filed Mar. 10, 2014, each of which is incorporated herein by reference in its entirety.

FIELD OF THE INVENTION

The invention relates to biomarkers and methods of diagnosing or monitoring schizophrenia, or a predisposition thereto.

BACKGROUND OF THE INVENTION

Diagnosis of schizophrenia has not changed over the last 100 years since Emil Kraepelin first defined the disease and is still based on evaluation of signs and symptoms in clinical interviews. If a patient does not acknowledge the occurrence of symptoms of psychosis, such as hallucinations and delusions, the disease can remain undiagnosed. In addition, some of the symptoms also occur in patients with mood and personality disorders and therefore misdiagnosis is a common occurrence. For example, Gonzalez-Pinto and co-workers found that approximately one-third of bipolar patients were diagnosed with schizophrenia (Bromet E. J. et al. (2005) *Schizophr. Bull.* 31(3):639-49). Another complication and reason for delay in diagnosis of schizophrenia is the insidious disease onset. Over the last two decades, the concept of prodromal schizophrenia, also referred to as ultra-high risk syndrome, has been a major focus of schizophrenia research. Research has shown that 20-30% of ultra-high risk individuals develop schizophrenia over a two to three year period (Fusar-Poli P. et al. (2012) *Arch. Gen. Psychiatry* 69(3):220-9). The prodromal syndrome is characterized on the basis of structured clinical interviews, which evaluate disturbances in perception, thought processing, language and attention (Fusar-Poli P. et al. (2014) *Annu. Rev. Clin. Psychol.*).

Early diagnosis of schizophrenia, ideally before or during the prodromal stages, would be beneficial for the outcome of patients. Long duration of untreated psychosis has been linked to poorer outcomes and there is evidence that early intervention or treatment can improve the outcome or even prevent the onset of schizophrenia (van der Gaag M. et al. (2013) *Schizophr. Res.* 149(1-3):56-62). The recent revision of the Diagnostic and Statistical Manual of Mental Disorders (DSM-5) has initiated discussion on the validity of the prodromal syndrome as a potential diagnostic category, which has now been listed in the appendix of DSM-5 as a "condition for further systematic study" (Tandon R. (2013) *Schizophr. Res.* 150(1):1-2). One critical concern is that approximately 70% of individuals who fulfill prodromal criteria do not develop schizophrenia and incorrect diagnosis would result in unwarranted treatment and stigma (Fusar-Poli P. et al. (2014) *Annu. Rev. Clin. Psychol.*).

Regulatory health authorities such as the Food and Drug Administration (FDA) have called for efforts to incorporate new methods such as biomarker applications to improve diagnosis and for delivery of more efficacious and safer drugs (Owens J. (2006) *Nat. Rev. Drug Discov.* 5(4):271). The FDA has defined three types of biomarkers: 1) exploratory biomarkers, 2) probable valid biomarkers and 3) known valid biomarkers (Goodsaid F. and Frueh F. W. (2007) *Environ. Mol. Mutagen.* 48(5):354-8). The third class is the most stringent as this requires replication of results at different sites, for cross-validation purposes.

A recently reported approach based on multiplexed immunoassay profiling, resulted in identification of a serum biomarker panel that could identify first-onset schizophrenia patients with an accuracy of 83% (Schwarz E. et al. (2012) *Mol. Psychiatry.* 17(5):494-502). However, this test was developed to differentiate schizophrenia patients from healthy controls, whereas psychiatrists place great clinical importance on development of blood tests that would help in the prediction of prodromal conversion and which could be used for differential diagnosis (e.g. differentiation between schizophrenia and affective psychosis).

Therefore, there is a need to develop an objective test, in particular a blood-based molecular biomarker test, for identification of schizophrenia prior to disease onset.

SUMMARY OF THE INVENTION

According to a first aspect of the invention, there is provided the use of Macrophage migration inhibitory factor (MIF) and Pancreatic polypeptide (PPP) as a specific panel of analyte biomarkers for the diagnosis or prognosis of schizophrenia, or predisposition thereto.

According to a further aspect of the invention, there is provided the use of Apolipoprotein H (ApoH), Apolipoprotein A1 (ApoA1), Macrophage migration inhibitory factor (MIF), Tenascin C (TNC), Interleukin-1 receptor antagonist (IL-1ra), Receptor for advanced glycosylation end products (RAGE), Interleukin-8 (IL-8), Haptoglobin, von Willebrand factor (VWF), Beta-2 microglobulin (B2M), Immunoglobulin A (IgA), Pancreatic polypeptide (PPP), Leptin, Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII) and Angiotensin-converting enzyme (ACE) as a specific panel of analyte biomarkers for the diagnosis or prognosis of schizophrenia, or predisposition thereto.

According to a further aspect of the invention, there is provided a method of diagnosing schizophrenia or predisposition in an individual thereto, comprising:
(a) quantifying the amounts of the analyte biomarkers as defined herein in a biological sample obtained from an individual;
(b) comparing the amounts of the analyte biomarkers in the biological sample with the amounts present in a normal control biological sample from a normal subject, such that a difference in the level of the analyte biomarkers in the biological sample is indicative of schizophrenia, or predisposition thereto.

According to a further aspect of the invention, there is provided a method of prognosing the development of schizophrenia in an individual, comprising:
(a) quantifying the amounts of the analyte biomarkers as defined herein in a biological sample obtained from an individual;
(b) comparing the amounts of the analyte biomarkers in the biological sample with the amounts present in a normal control biological sample from a normal subject, such that a difference in the level of the analyte biomarkers in the biological sample is indicative that the individual will develop schizophrenia According to a further aspect of the invention, there is provided a method of monitoring efficacy of a therapy in a subject having, suspected of having, or of being predisposed to schizophrenia, comprising detecting and/or quantifying, in a sample from said subject, the analyte biomarkers as defined herein.

A further aspect of the invention provides ligands, such as naturally occurring or chemically synthesised compounds, capable of specific binding to the peptide biomarker. A ligand according to the invention may comprise a peptide, an antibody or a fragment thereof, or an aptamer or oligonucleotide, capable of specific binding to the peptide biomarker. The antibody can be a monoclonal antibody or a fragment thereof capable of specific binding to the peptide biomarker. A ligand according to the invention may be labelled with a detectable marker, such as a luminescent, fluorescent or radioactive marker; alternatively or additionally a ligand according to the invention may be labelled with an affinity tag, e.g. a biotin, avidin, streptavidin or His (e.g. hexa-His) tag.

A biosensor according to the invention may comprise the peptide biomarker or a structural/shape mimic thereof capable of specific binding to an antibody against the peptide biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the peptide. In these uses, the detection and/or quantification can be performed on a biological sample such as from the group consisting of whole blood, blood serum, plasma, CSF, urine, saliva, or other bodily fluid, breath, e.g. as condensed breath, or an extract or purification therefrom, or dilution thereof.

Diagnostic, prognostic or monitoring kits are provided for performing methods of the invention. Such kits will suitably comprise a ligand according to the invention, for detection and/or quantification of the peptide biomarker, and/or a biosensor, and/or an array as described herein, optionally together with instructions for use of the kit.

According to a further aspect of the invention, there is provided the use of a kit comprising a biosensor capable of detecting and/or quantifying the analyte biomarkers as defined herein for monitoring, prognosing or diagnosing schizophrenia or a predisposition thereto.

Biomarkers for schizophrenia or other psychotic disorder are essential targets for discovery of novel targets and drug molecules that retard or halt progression of the disorder. As the level of the peptide biomarker is indicative of disorder and of drug response, the biomarker is useful for identification of novel therapeutic compounds in in vitro and/or in vivo assays. Biomarkers of the invention can be employed in methods for screening for compounds that modulate the activity of the peptide.

Thus, in a further aspect of the invention, there is provided the use of a ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the peptide in a subject, comprising administering a test substance to a subject animal and detecting and/or quantifying the level of the peptide biomarker present in a test sample from the subject.

In general, when a doctor or other medical practitioner is apprised that a patient is suffering from schizophrenia, the practitioner will treat the individual to alleviate the causes or symptoms of the disorder. Thus, according to a further aspect of the invention, there is provided a method for treating schizophrenia. Methods of treatment may comprise treating a patient with anti-psychotic drugs and/or non-drug therapies. Treatment may be based upon a diagnosis or suspicion of schizophrenia derived from the methods, analyte biomarkers and specific panels of analyte biomarkers as described herein.

The results of any analyses according to the invention will often be communicated to physicians and/or patients (or other interested parties such as researchers) in a transmittable form that can be communicated or transmitted to any of the above parties. Therefore, according to a further aspect of the invention, there is provided systems for diagnosing and treating schizophrenia. These systems may comprise sample analyzers, computers and software as described herein.

DETAILED DESCRIPTION OF THE INVENTION

Figure 1:
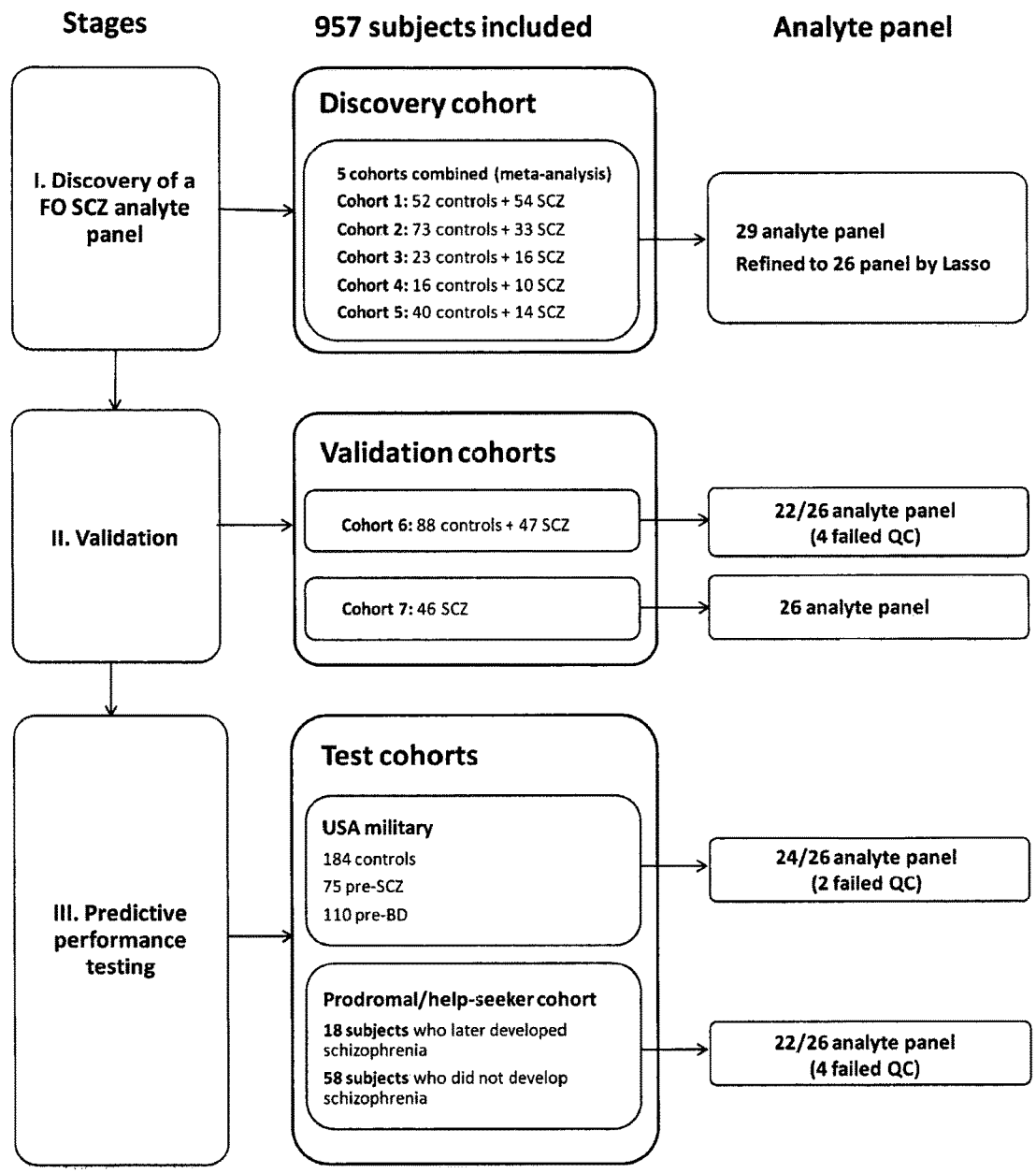
FIG. 1: Workflow showing subject inclusion and biomarker panel selection/testing.

The results provided herein describe an extensive study of a blood-based molecular biomarker panel for schizophrenia. In particular, serum analyte changes were identified and validated in first-onset drug-naïve schizophrenia patients. A particular objective was to determine whether this panel could predict schizophrenia conversion in individuals presenting with prodromal symptoms, as well as in non-psychotic psychiatric help-seekers. A further objective was to determine whether the panel could predict schizophrenia onset in individuals prior to the onset of psychiatric symptoms.

Biomarkers

The term "biomarker" means a distinctive biological or biologically derived indicator of a process, event, or condition. Peptide biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

Data is provided herein which demonstrates that the specific panel of analyte biomarkers described herein, contains statistically significant biomarkers for the diagnosis and prognosis of schizophrenia.

In particular, the biomarker panels described herein have been shown to have good to excellent performance in predicting patients who later converted from prodromal syndrome to schizophrenia, as well as predicting development of schizophrenia who did not display overt psychopathology at the time of sample collection.

Therefore, according to a first aspect of the invention, there is provided the use of Macrophage migration inhibitory factor (MIF) and Pancreatic polypeptide (PPP) as a specific panel of biomarkers for the diagnosis or prognosis of schizophrenia, or predisposition thereto.

Data is provided herein which demonstrates that this panel of two biomarkers is successful at discriminating schizophrenia patients from healthy controls in the discovery cohort (i.e. cohorts 1-5) with an AUC of 0.79 (see Table 5).

In one embodiment, the panel additionally comprises one or more analyte biomarkers selected from: Apolipoprotein H (ApoH), Apolipoprotein A1 (ApoA1), Tenascin C (TNC), Interleukin-1 receptor antagonist (IL-1ra), Receptor for advanced glycosylation end products (RAGE), Interleukin-8 (IL-8), Haptoglobin, von Willebrand factor (VWF), Beta-2 microglobulin (B2M), Immunoglobulin A (IgA), Leptin, Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII), Angiotensin-converting enzyme (ACE), Carcinoembryonic antigen (CEA), Interleukin-10 (IL-10), Alpha-2 Macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin.

According to a further aspect of the invention, there is provided the use of Macrophage migration inhibitory factor (MIF) and Pancreatic polypeptide (PPP) as a specific panel of biomarkers for the diagnosis of schizophrenia, or predisposition thereto.

In one embodiment, the panel additionally comprises Leptin. Therefore, it will be understood that according to a further aspect of the invention, there is provided the use of Macrophage migration inhibitory factor (MIF), Pancreatic polypeptide (PPP) and Leptin as a specific panel of biomarkers for the diagnosis or prognosis of schizophrenia, or predisposition thereto.

Data is provided herein which demonstrates that this panel of three biomarkers is successful at discriminating schizophrenia patients from healthy controls in the discovery cohort with an AUC of 0.81 (see Table 5).

In one embodiment, the panel additionally comprises one or more analyte biomarkers selected from: Apolipoprotein H (ApoH), Apolipoprotein A1 (ApoA1), Tenascin C (TNC), Interleukin-1 receptor antagonist (IL-1ra), Receptor for advanced glycosylation end products (RAGE), Interleukin-8 (IL-8), Haptoglobin, von Willebrand factor (VWF), Beta-2 microglobulin (B2M), Immunoglobulin A (IgA), Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII), Angiotensin-converting enzyme (ACE), Carcinoembryonic antigen (CEA), Interleukin-10 (IL-10), Alpha-2 Macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin.

According to a further aspect of the invention, there is provided the use of Macrophage migration inhibitory factor (MIF), Pancreatic polypeptide (PPP) and Leptin as a specific panel of biomarkers for the diagnosis of schizophrenia, or predisposition thereto.

In one embodiment, the panel additionally comprises Factor VII (FVII), Haptoglobin, Receptor for advanced glycosylation end products (RAGE) and Tenascin C (TNC). Therefore, it will be understood that according to a further aspect of the invention, there is provided the use of Macrophage migration inhibitory factor (MIF), Pancreatic polypeptide (PPP), Leptin, Factor VII (FVII), Haptoglobin, Receptor for advanced glycosylation end products (RAGE) and Tenascin C (TNC) as a specific panel of biomarkers for the diagnosis or prognosis of schizophrenia, or predisposition thereto.

Data is provided herein which demonstrates that this panel of seven biomarkers is successful at discriminating schizophrenia patients from healthy controls in the discovery cohort with an AUC of 0.89 and the Santander cohort (i.e. cohort 6) with an AUC of 0.90 (see Table 5).

In one embodiment, the panel additionally comprises one or more analyte biomarkers selected from: Apolipoprotein H (ApoH), Apolipoprotein A1 (ApoA1), Interleukin-1 receptor antagonist (IL-1ra), Interleukin-8 (IL-8), von Willebrand factor (VWF), Beta-2 microglobulin (B2M), Immunoglobulin A (IgA), Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Angiotensin-converting enzyme (ACE), Carcinoembryonic antigen (CEA), Interleukin-10 (IL-10), Alpha-2 Macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin.

According to a further aspect of the invention, there is provided the use of Macrophage migration inhibitory factor (MIF), Pancreatic polypeptide (PPP), Leptin, Factor VII (FVII), Haptoglobin, Receptor for advanced glycosylation end products (RAGE) and Tenascin C (TNC) as a specific panel of biomarkers for the diagnosis of schizophrenia, or predisposition thereto.

In one embodiment, the panel additionally comprises AXL receptor tyrosine kinase (AXL), Follicle-stimulating hormone (FSH), Insulin-like growth factor-binding protein 2 (IGFBP2) and Interleukin-1 receptor antagonist (IL-1ra). Therefore, it will be understood that according to a further aspect of the invention, there is provided the use of Macrophage migration inhibitory factor (MIF), Pancreatic polypeptide (PPP), Leptin, Factor VII (FVII), Haptoglobin, Receptor for advanced glycosylation end products (RAGE), Tenascin C (TNC), AXL receptor tyrosine kinase (AXL), Follicle-stimulating hormone (FSH), Insulin-like growth factor-binding protein 2 (IGFBP2) and Interleukin-1 receptor antagonist (IL-1ra) as a specific panel of biomarkers for the diagnosis or prognosis of schizophrenia, or predisposition thereto.

Data is provided herein which demonstrates that this panel of eleven biomarkers is successful at discriminating schizophrenia patients from healthy controls in the discovery cohort and the Santander cohort with an AUC of 0.90 and 0.93, respectively (see Table 5).

In one embodiment, the panel additionally comprises one or more analyte biomarkers selected from: Apolipoprotein H (ApoH), Apolipoprotein A1 (ApoA1), Interleukin-8 (IL-8), von Willebrand factor (VWF), Beta-2 microglobulin (B2M), Immunoglobulin A (IgA), Testosterone (Total), Thyroid stimulating hormone (TSH), Stem Cell Factor (SCF), Angiotensin-converting enzyme (ACE), Carcinoembryonic antigen (CEA), Interleukin-10 (IL-10), Alpha-2 Macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin.

According to a further aspect of the invention, there is provided the use of Macrophage migration inhibitory factor (MIF), Pancreatic polypeptide (PPP), Leptin, Factor VII (FVII), Haptoglobin, Receptor for advanced glycosylation end products (RAGE), Tenascin C (TNC), AXL receptor tyrosine kinase (AXL), Follicle-stimulating hormone (FSH), Insulin-like growth factor-binding protein 2 (IGFBP2) and Interleukin-1 receptor antagonist (IL-1ra) as a specific panel of biomarkers for the diagnosis of schizophrenia, or predisposition thereto.

In one embodiment, the panel additionally comprises Beta-2 microglobulin (B2M), Interleukin-8 (IL-8), Stem Cell Factor (SCF) and von Willebrand factor (VWF). Therefore, it will be understood that according to a further aspect of the invention, there is provided the use of Macrophage migration inhibitory factor (MIF), Pancreatic polypeptide (PPP), Leptin, Factor VII (FVII), Haptoglobin, Receptor for advanced glycosylation end products (RAGE), Tenascin C (TNC), AXL receptor tyrosine kinase (AXL), Follicle-stimulating hormone (FSH), Insulin-like growth factor-binding protein 2 (IGFBP2), Interleukin-1 receptor antagonist (IL-1ra), Beta-2 microglobulin (B2M), Interleukin-8 (IL-8), Stem Cell Factor (SCF) and von Willebrand factor (VWF) as a specific panel of biomarkers for the diagnosis or prognosis of schizophrenia, or predisposition thereto.

Data is provided herein which demonstrates that this panel of fifteen biomarkers is successful at discriminating schizophrenia patients from healthy controls in the discovery cohort and the Santander cohort with an AUC of 0.92 and 0.94, respectively (see Table 5).

In one embodiment, the panel additionally comprises one or more analyte biomarkers selected from: Apolipoprotein H (ApoH), Apolipoprotein A1 (ApoA1), Immunoglobulin A (IgA), Testosterone (Total), Thyroid stimulating hormone (TSH), Angiotensin-converting enzyme (ACE), Carcinoembryonic antigen (CEA), Interleukin-10 (IL-10), Alpha-2 Macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin.

According to a further aspect of the invention, there is provided the use of Macrophage migration inhibitory factor (MIF), Pancreatic polypeptide (PPP), Leptin, Factor VII (FVII), Haptoglobin, Receptor for advanced glycosylation end products (RAGE), Tenascin C (TNC), AXL receptor tyrosine kinase (AXL), Follicle-stimulating hormone (FSH), Insulin-like growth factor-binding protein 2 (IGFBP2), Interleukin-1 receptor antagonist (IL-1ra), Beta-2 microglobulin (B2M), Interleukin-8 (IL-8), Stem Cell Factor (SCF) and von Willebrand factor (VWF) as a specific panel of biomarkers for the diagnosis of schizophrenia, or predisposition thereto.

In one embodiment, the panel additionally comprises Angiotensin-converting enzyme (ACE), Apolipoprotein H (ApoH) and Immunoglobulin A (IgA). Therefore, it will be understood that according to a further aspect of the invention, there is provided the use of Macrophage migration inhibitory factor (MIF), Pancreatic polypeptide (PPP), Leptin, Factor VII (FVII), Haptoglobin, Receptor for advanced glycosylation end products (RAGE), Tenascin C (TNC), AXL receptor tyrosine kinase (AXL), Follicle-stimulating hormone (FSH), Insulin-like growth factor-binding protein 2 (IGFBP2), Interleukin-1 receptor antagonist (IL-1ra), Beta-2 microglobulin (B2M), Interleukin-8 (IL-8), Stem Cell Factor (SCF), von Willebrand factor (VWF), Angiotensin-converting enzyme (ACE), Apolipoprotein H (ApoH) and Immunoglobulin A (IgA) as a specific panel of biomarkers for the diagnosis or prognosis of schizophrenia, or predisposition thereto.

Data is provided herein which demonstrates that this panel of eighteen biomarkers is successful at discriminating schizophrenia patients from healthy controls in the discovery cohort and the Santander cohort with an AUC of 0.92 and 0.96, respectively (see Table 5).

In one embodiment, the panel additionally comprises one or more analyte biomarkers selected from: Apolipoprotein A1 (ApoA1), Testosterone (Total), Thyroid stimulating hormone (TSH), Carcinoembryonic antigen (CEA), Interleukin-10 (IL-10), Alpha-2 Macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin.

In one embodiment, the panel additionally comprises Apolipoprotein A1 (ApoAI) and Testosterone (total). Therefore, it will be understood that according to a further aspect of the invention, there is provided the use of Macrophage migration inhibitory factor (MIF), Pancreatic polypeptide (PPP), Leptin, Factor VII (FVII), Haptoglobin, Receptor for advanced glycosylation end products (RAGE), Tenascin C (TNC), AXL receptor tyrosine kinase (AXL), Follicle-stimulating hormone (FSH), Insulin-like growth factor-binding protein 2 (IGFBP2), Interleukin-1 receptor antagonist (IL-1ra), Beta-2 microglobulin (B2M), Interleukin-8 (IL-8), Stem Cell Factor (SCF), von Willebrand factor (VWF), Angiotensin-converting enzyme (ACE), Apolipoprotein H (ApoH), Immunoglobulin A (IgA), Apolipoprotein A1 (ApoAI) and Testosterone (total) as a specific panel of analyte biomarkers for the diagnosis or prognosis of schizophrenia, or predisposition thereto.

Data is provided herein which demonstrates that this panel of twenty biomarkers is successful at discriminating schizophrenia patients from healthy controls in the discovery cohort and the Santander cohort with an AUC of 0.93 and 0.97, respectively (see Table 5).

In one embodiment, the panel additionally comprises one or more analyte biomarkers selected from: Thyroid stimulating hormone (TSH), Carcinoembryonic antigen (CEA), Interleukin-10 (IL-10), Alpha-2 Macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin.

In one embodiment, the panel additionally comprises Thyroid stimulating hormone (TSH). Therefore, it will be understood that according to a further aspect of the invention, there is provided the use of Apolipoprotein H (ApoH), Apolipoprotein A1 (ApoA1), Macrophage migration inhibitory factor (MIF), Tenascin C (TNC), Interleukin-1 receptor antagonist (IL-1ra), Receptor for advanced glycosylation end products (RAGE), Interleukin-8 (IL-8), Haptoglobin, von Willebrand factor (VWF), Beta-2 microglobulin (B2M), Immunoglobulin A (IgA), Pancreatic polypeptide (PPP), Leptin, Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII) and Angiotensin-converting enzyme (ACE) as a specific panel of analyte biomarkers for the diagnosis or prognosis of schizophrenia, or predisposition thereto.

Data is provided herein which demonstrates that this panel of twenty one biomarkers is successful at discriminating schizophrenia patients from healthy controls (AUC from 0.90 to 0.97) as well as prodromal converters from non-converters (AUC of 0.80) (see Table 5).

In one embodiment, the panel additionally comprises one or more analyte biomarkers selected from: Carcinoembryonic antigen (CEA), Interleukin-10 (IL-10), Alpha-2 macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin, in particular, Carcinoembryonic antigen (CEA), Interleukin-10 (IL-10), Alpha-2 macroglobulin (A2M), Serum glutamic oxaloacetic transaminase (SGOT) and Interleukin-13 (IL-13).

In one embodiment, the panel additionally comprises Alpha-2 macroglobulin (A2M). Therefore, it will be understood that according to a further aspect of the invention, there is provided the use of Apolipoprotein H (ApoH), Apolipoprotein A1 (ApoA1), Macrophage migration inhibitory factor (MIF), Tenascin C (TNC), Interleukin-1 receptor antagonist (IL-1ra), Receptor for advanced glycosylation end products (RAGE), Interleukin-8 (IL-8), Haptoglobin, von Willebrand factor (VWF), Beta-2 microglobulin (B2M), Immunoglobulin A (IgA), Pancreatic polypeptide (PPP), Leptin, Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII), Angiotensin-converting enzyme (ACE) and Alpha-2 macroglobulin (A2M) as a specific panel of analyte biomarkers for the diagnosis or prognosis of schizophrenia, or predisposition thereto.

Data is provided herein which demonstrates that this panel of biomarkers is successful at discriminating schizophrenia patients from healthy controls in cohort 6. For example, these twenty two most reproducible markers resulted in an average assay sensitivity and specificity of 87% and 97%, respectively, with a ROC-AUC of 0.97 (see FIG. 3). Furthermore, this panel was able to predict whether a patient would convert from prodromal syndrome to schizophrenia with an AUC of 0.82 (see Table 3).

In one embodiment, the panel additionally comprises one or more analyte biomarkers selected from: Carcinoembryonic antigen (CEA), Interleukin-10 (IL-10), Serum glutamic oxaloacetic transaminase (SGOT), Interleukin-13 (IL-13), Chromogranin-A (CGA), Vascular cell adhesion molecule-1 (VCAM-1) and Eotaxin, in particular, Carcinoembryonic antigen (CEA), Interleukin-10 (IL-10), Serum glutamic oxaloacetic transaminase (SGOT) and Interleukin-13 (IL-13).

According to a further aspect of the invention, there is provided the use of Apolipoprotein H (ApoH), Apolipoprotein A1 (ApoA1), Macrophage migration inhibitory factor (MIF), Tenascin C (TNC), Interleukin-1 receptor antagonist (IL-1ra), Receptor for advanced glycosylation end products (RAGE), Interleukin-8 (IL-8), Haptoglobin, von Willebrand factor (VWF), Beta-2 microglobulin (B2M), Immunoglobulin A (IgA), Pancreatic polypeptide (PPP), Leptin, Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII), Angiotensin-converting enzyme (ACE), Carcinoembryonic antigen (CEA), Serum glutamic oxaloacetic transaminase (SGOT) and Interleukin-13 (IL-13) as a specific panel of analyte biomarkers for the diagnosis or prognosis of schizophrenia, or predisposition thereto.

Data is provided herein which demonstrates that this panel of biomarkers is successful at predicting the development of schizophrenia in personnel who were sampled 30 days or more prior to manifestation of symptoms. For example, these twenty four most reproducible markers resulted in an average assay sensitivity and specificity of 92% and 78%, respectively, with a ROC-AUC of 0.91 (see FIG. 4).

In one embodiment, the panel additionally comprises one or more analyte biomarkers selected from: Interleukin-10 (IL-10), Alpha-2 macroglobulin (A2M), Chromogranin-A (CGA), Vascular cell adhesion molecule-1 (VCAM-1) and Eotaxin, in particular, Interleukin-10 (IL-10) and Alpha-2 macroglobulin (A2M).

According to a further aspect of the invention, there is provided the use of Apolipoprotein H (ApoH), Apolipoprotein A1 (ApoA1), Macrophage migration inhibitory factor (MIF), Tenascin C (TNC), Interleukin-1 receptor antagonist (IL-1ra), Receptor for advanced glycosylation end products (RAGE), Interleukin-8 (IL-8), Haptoglobin, von Willebrand factor (VWF), Beta-2 microglobulin (B2M), Immunoglobulin A (IgA), Pancreatic polypeptide (PPP), Leptin, Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII), Angiotensin-converting enzyme (ACE), Carcinoembryonic antigen (CEA), Interleukin-10 (IL-10), Alpha-2 Macroglobulin (A2M), Serum glutamic oxaloacetic transaminase (SGOT) and Interleukin-13 (IL-13) as a specific panel of analyte biomarkers for the diagnosis or prognosis of schizophrenia, or predisposition thereto.

Data is provided herein which demonstrates that this panel of biomarkers is successful at discriminating schizophrenia patients from healthy controls in cohorts 1-5. For example, these twenty six most reproducible markers resulted in an average assay sensitivity and specificity of 90% and 90%, respectively, with a ROC-AUC of 0.96 (see Table 2 and FIG. 2).

In one embodiment, the panel additionally comprises one or more analyte biomarkers selected from: Chromogranin-A (CGA), Vascular cell adhesion molecule-1 (VCAM-1) and Eotaxin.

According to a further aspect of the invention, there is provided the use of Apolipoprotein H (ApoH), Apolipoprotein A1 (ApoA1), Macrophage migration inhibitory factor (MIF), Tenascin C (TNC), Interleukin-1 receptor antagonist (IL-1ra), Receptor for advanced glycosylation end products (RAGE), Interleukin-8 (IL-8), Haptoglobin, von Willebrand factor (VWF), Beta-2 microglobulin (B2M), Immunoglobulin A (IgA), Pancreatic polypeptide (PPP), Leptin, Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII), Angiotensin-converting enzyme (ACE), Carcinoembryonic antigen (CEA), Interleukin-10 (IL-10), Alpha-2 Macroglobulin (A2M), Serum glutamic oxaloacetic transaminase (SGOT), Interleukin-13 (IL-13), Chromogranin-A (CGA), Vascular cell adhesion molecule-1 (VCAM-1) and Eotaxin as a specific panel of analyte biomarkers for the diagnosis or prognosis of schizophrenia, or predisposition thereto.

Data is provided herein which demonstrates that this panel of biomarkers is successful at discriminating schizophrenia patients from healthy controls in cohorts 1-5. For example, these twenty nine most reproducible markers resulted in an average assay sensitivity and specificity of 91% and 88%, respectively, with a ROC-AUC of 0.96 (see FIG. 2).

Differential Diagnosis

The results presented herein have also demonstrated that the biomarker panel described herein has high specificity for schizophrenia. In particular, a lower performance was achieved (AUC=0.72) when the panel was used to test samples from individuals who were later diagnosed with bipolar disorder. Therefore, according to a further aspect of the invention, the biomarker panels described herein may be used as a specific panel of biomarkers for the differential diagnosis of schizophrenia or other psychotic disorder from a further psychiatric disorder, such as a neuropsychiatric disorder.

It will be appreciated that the term "differential diagnosis" refers to the positive diagnosis of schizophrenia or other psychotic disorder from that of a further psychiatric disorder, such as a neuropsychiatric disorder.

Non-limiting examples of psychiatric disorders include: mood disorders such as depression, major depressive disorder, treatment resistant depression, mania, cyclothymic disorder and bipolar disorders (including bipolar disorder in manic, depressive and euthymic phases); anxiety disorders such as generalized anxiety disorder, obsessive-compulsive disorder (OCD), panic attacks and panic disorder, phobic disorders, stress disorders; dissociative disorders such as depersonalization disorder, dissociative amnesia, dissociative fugue, dissociative identity disorder; drug use and dependence; eating disorders such as anorexia nervosa, binge eating disorder and bulimia nervosa; personality disorders; sexuality and sexual disorders such as gender identity disorder and transsexualism and paraphilias; somatoform and factitious disorders such as body dysmorphic disorder, conversion disorder, hypochondriasis, Munchausen syndrome, pain disorder and somatization disorder; Asperger syndrome or suicidal behavior.

In one embodiment, the further psychiatric disorder is selected from one or both of bipolar disorder and major depressive disorder, in particular bipolar disorder.

References herein to "other psychotic disorder" relate to any appropriate psychotic disorder according to DSM-IV *Diagnostic and Statistical Manual of Mental Disorders,* 4th edition, American Psychiatric Assoc., Washington, D.C., 2000. In one particular embodiment, the other psychotic disorder is a psychotic disorder related to schizophrenia.

Methods of Diagnosis, Prognosis or Monitoring

According to a further aspect of the invention, there is provided a method of diagnosing schizophrenia or predisposition in an individual thereto, comprising:

(a) quantifying the amounts of the analyte biomarkers as defined herein in a biological sample obtained from an individual;

(b) comparing the amounts of the analyte biomarkers in the biological sample with the amounts present in a normal control biological sample from a normal subject, such that a difference in the level of the analyte biomarkers in the biological sample is indicative of schizophrenia, or predisposition thereto.

According to a further aspect of the invention, there is provided a method of prognosing the development of schizophrenia in an individual, comprising:

(a) quantifying the amounts of the analyte biomarkers as defined herein in a biological sample obtained from an individual;

(b) comparing the amounts of the analyte biomarkers in the biological sample with the amounts present in a normal control biological sample from a normal subject, such that a difference in the level of the analyte biomarkers in the biological sample is indicative that the individual will develop schizophrenia.

It should be noted that references to biomarker amounts or levels also include references to a biomarker range.

It will be appreciated that references herein to "difference in the level" refer to either a higher or lower level of the biomarker(s) in the test biological sample compared with the reference sample(s).

In one embodiment, the higher or lower level is a <1 fold difference relative to the reference sample, such as a fold difference of 0.9, 0.8, 0.7, 0.6, 0.5, 0.4, 0.3, 0.2, 0.1, 0.05, 0.01 or any ranges therebetween. In one embodiment, the lower level is between a 0.1 and 0.9 fold difference, such as between a 0.2 and 0.5 fold difference, relative to the reference sample.

In one embodiment, the higher or lower level is a >1 fold difference relative to the reference sample, such as a fold difference of 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 15 or 20 or any ranges therebetween. In one embodiment, the higher level is between a 1 and 15 fold difference, such as between a 2 and 10 fold difference, relative to the reference sample.

In one embodiment, the individual is a drug naïve schizophrenia patient (e.g. a first onset drug-naïve patient). In a further embodiment, the individual is first-onset or recent-onset drug naïve schizophrenia patient. In a yet further embodiment, the individual is an un-medicated schizophrenic patient.

It will be understood that the term "drug naïve" patients includes patients which have not previously been diagnosed or medicated for schizophrenia. It will also be understood that the term "un-medicated" refers to patients which have not been taking medication for schizophrenia (i.e. antipsychotic medication) for at least 1 year, for example for at least 2, 3, 4, 5, 6, 7, 8, 9 or 10 years, in particular for at least 3 years.

In one embodiment, the individual has prodromal syndrome.

References to "prodromal syndrome" as used herein refer to the period of decreased functioning in a patient that precedes the onset of schizophrenia. Prodromal syndrome may be diagnosed on the basis of structured clinical interviews (see Fusar-Poli P. et al. (2014) *Annu. Rev. Clin. Psychol.*).

Early diagnosis of schizophrenia, ideally before or during the prodromal stages, would be beneficial for the outcome of patients because long duration of untreated psychosis has been linked to poorer outcomes. However, approximately 70% of individuals who fulfill prodromal criteria do not develop schizophrenia and incorrect diagnosis could result in unwarranted treatment and stigma. Therefore, the panels described herein can be used to accurately predict whether the patient will develop schizophrenia (i.e. prognosis) so that they can benefit from early treatment.

According to a further aspect of the invention, there is provided a method of monitoring efficacy of a therapy in a subject having, suspected of having, or of being predisposed to schizophrenia, comprising detecting and/or quantifying, in a sample from said subject, the analyte biomarkers as defined herein.

Monitoring methods of the invention can be used to monitor onset, progression, stabilisation, amelioration and/or remission.

In methods of diagnosing, prognosing or monitoring according to the invention, detecting and/or quantifying the peptide biomarker in a biological sample from a test subject may be performed on two or more occasions. Comparisons may be made between the level of biomarker in samples taken on two or more occasions. Assessment of any change in the level of the peptide biomarker in samples taken on two or more occasions may be performed. Modulation of the peptide biomarker level is useful as an indicator of the state of schizophrenia or other psychotic disorder or predisposition thereto. An increase in the level of the biomarker, over time is indicative of onset or progression, i.e. worsening of this disorder, whereas a decrease in the level of the peptide biomarker indicates amelioration or remission of the disorder, or vice versa.

A method of diagnosis or prognosis of or monitoring according to the invention may comprise quantifying the peptide biomarker in a test biological sample from a test subject and comparing the level of the peptide present in said test sample with one or more controls.

The control used in a method of the invention can be one or more control(s) selected from the group consisting of: the level of biomarker peptide found in a normal control sample from a normal subject, a normal biomarker peptide level; a normal biomarker peptide range, the level in a sample from a subject with schizophrenia or other psychotic disorder, or a diagnosed predisposition thereto; schizophrenia or other psychotic disorder biomarker peptide level, or schizophrenia or other psychotic disorder biomarker peptide range.

In one embodiment, the biomarker panel described herein may be used in conjunction with current methods of diagnosis (i.e. structured interviews and/or psychiatric assessment). The use of both tests will aid in earlier and more accurate diagnosis of schizophrenia. In a further embodiment, the biomarker panel described herein may be used in conjunction with the Comprehensive Assessment of At-Risk Mental State (CAARMS). Data is provided herein which shows that diagnostic performance was improved by incorporation of CAARMS positive subscale scores (see Table 3).

Also provided is a method of monitoring efficacy of a therapy for schizophrenia in a subject having such a disorder, suspected of having such a disorder, or of being predisposed thereto, comprising detecting and/or quantifying the peptide present in a biological sample from said subject. In monitoring methods, test samples may be taken on two or more occasions. The method may further comprise comparing the level of the biomarker present in the test sample with one or more reference(s) and/or with one or more previous test sample(s) taken earlier from the same test subject, e.g. prior to commencement of therapy, and/or from the same test subject at an earlier stage of therapy. The method may comprise detecting a change in the level of the biomarker in test samples taken on different occasions.

In one embodiment, the method comprises comparing the amount of biomarker(s) in said test biological sample with the amount present in one or more samples taken from said individual prior to commencement of treatment, and/or one or more samples taken from said individual during treatment.

For biomarkers which are increased in individuals with schizophrenia, a higher level of the peptide biomarker in the test sample relative to the level in the normal control is indicative of the presence of schizophrenia or other psychotic disorder, or predisposition thereto; an equivalent or lower level of the peptide in the test sample relative to the normal control is indicative of absence of schizophrenia and/or absence of a predisposition thereto.

For biomarkers which are decreased in individuals with schizophrenia, a lower level of the peptide biomarker in the test sample relative to the level in the normal control is indicative of the presence of schizophrenia or other psychotic disorder, or predisposition thereto; an equivalent or lower level of the peptide in the test sample relative to the normal control is indicative of absence of schizophrenia and/or absence of a predisposition thereto.

The term "diagnosis" as used herein encompasses identification, confirmation, and/or characterisation of schizophrenia or other psychotic disorder, or predisposition thereto. The term "prognosis" as used herein encompasses the prediction of whether a patient it likely to develop schizophrenia or other psychotic disorder. By "predisposition" it is meant that a subject does not currently present with the disorder, but is liable to be affected by the disorder in time.

Methods of monitoring and of diagnosis or prognosis according to the invention are useful to confirm the existence of a disorder, or predisposition thereto; to monitor development of the disorder by assessing onset and progression, or to assess amelioration or regression of the disorder. Methods of monitoring and of diagnosis or prognosis are also useful in methods for assessment of clinical screening, choice of therapy, evaluation of therapeutic benefit, i.e. for drug screening and drug development.

Efficient diagnosis, prognosis and monitoring methods provide very powerful "patient solutions" with the potential for improved prognosis, by establishing the correct diagnosis, allowing rapid identification of the most appropriate treatment (thus lessening unnecessary exposure to harmful drug side effects), reducing "down-time" and relapse rates.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following therapy for schizophrenia. Samples can be taken at intervals over the remaining life, or a part thereof, of a subject.

The term "detecting" as used herein means confirming the presence of the peptide biomarker present in the sample. Quantifying the amount of the biomarker present in a sample may include determining the concentration of the peptide biomarker present in the sample. Detecting and/or quantifying may be performed directly on the sample, or indirectly on an extract therefrom, or on a dilution thereof.

In alternative aspects of the invention, the presence of the peptide biomarker is assessed by detecting and/or quantifying antibody or fragments thereof capable of specific binding to the biomarker that are generated by the subject's body in response to the peptide and thus are present in a biological sample from a subject having schizophrenia or a predisposition thereto.

Detecting and/or quantifying can be performed by any method suitable to identify the presence and/or amount of a specific protein in a biological sample from a patient or a purification or extract of a biological sample or a dilution thereof. In methods of the invention, quantifying may be performed by measuring the concentration of the peptide biomarker in the sample or samples. Biological samples that may be tested in a method of the invention include whole blood, blood serum, plasma, cerebrospinal fluid (CSF), urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner. IT will be understood that methods of the invention may be performed in vitro.

In one embodiment, the biological sample is whole blood, blood serum or plasma, such as blood serum.

Detection and/or quantification of peptide biomarkers may be performed by detection of the peptide biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length.

In one embodiment, the biomarker defined herein may be replaced by a molecule, or a measurable fragment of the molecule, found upstream or downstream of the biomarker in a biological pathway.

Methods of Detection

As used herein, the term "biosensor" means anything capable of detecting the presence of the biomarker. Examples of biosensors are described herein.

Biosensors according to the invention may comprise a ligand or ligands, as described herein, capable of specific binding to the peptide biomarker. Such biosensors are useful in detecting and/or quantifying a peptide of the invention.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods according to the invention may comprise analysing a sample of blood serum by SELDI-TOF or MALDI-TOF to detect the presence or level of the peptide biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the peptide biomarkers may be performed using an immunological method, involving an antibody, or a fragment thereof capable of specific binding to the peptide biomarker. Suitable immunological methods include sandwich immunoassays, such as sandwich ELISA, in which the detection of the peptide biomarkers is performed using two antibodies which recognize different epitopes on a peptide biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

Immunological methods in accordance with the invention may be based, for example, on any of the following methods.

Immunoprecipitation is the simplest immunoassay method; this measures the quantity of precipitate, which forms after the reagent antibody has incubated with the sample and reacted with the target antigen present therein to form an insoluble aggregate. Immunoprecipitation reactions may be qualitative or quantitative.

In particle immunoassays, several antibodies are linked to the particle, and the particle is able to bind many antigen molecules simultaneously. This greatly accelerates the speed of the visible reaction. This allows rapid and sensitive detection of the biomarker.

In immunonephelometry, the interaction of an antibody and target antigen on the biomarker results in the formation of immune complexes that are too small to precipitate. However, these complexes will scatter incident light and this can be measured using a nephelometer. The antigen, i.e. biomarker, concentration can be determined within minutes of the reaction.

Radioimmunoassay (RIA) methods employ radioactive isotopes such as $I^{125}$ to label either the antigen or antibody. The isotope used emits gamma rays, which are usually measured following removal of unbound (free) radiolabel. The major advantages of RIA, compared with other immunoassays, are higher sensitivity, easy signal detection, and well-established, rapid assays. The major disadvantages are the health and safety risks posed by the use of radiation and the time and expense associated with maintaining a licensed radiation safety and disposal program. For this reason, RIA has been largely replaced in routine clinical laboratory practice by enzyme immunoassays.

Enzyme (EIA) immunoassays were developed as an alternative to radioimmunoassays (RIA). These methods use an enzyme to label either the antibody or target antigen. The sensitivity of EIA approaches that of RIA, without the danger posed by radioactive isotopes. One of the most widely used EIA methods for detection is the enzyme-linked immunosorbent assay (ELISA). ELISA methods may use two antibodies one of which is specific for the target antigen and the other of which is coupled to an enzyme, addition of the substrate for the enzyme results in production of a chemiluminescent or fluorescent signal.

Fluorescent immunoassay (FIA) refers to immunoassays which utilize a fluorescent label or an enzyme label which acts on the substrate to form a fluorescent product. Fluorescent measurements are inherently more sensitive than colorimetric (spectrophotometric) measurements. Therefore, FIA methods have greater analytical sensitivity than EIA methods, which employ absorbance (optical density) measurement.

Chemiluminescent immunoassays utilize a chemiluminescent label, which produces light when excited by chemical energy; the emissions are measured using a light detector.

Immunological methods according to the invention can thus be performed using well-known methods. Any direct (e.g., using a sensor chip) or indirect procedure may be used in the detection of the peptide biomarker of the invention.

The Biotin-Avidin or Biotin-Streptavidin systems are generic labelling systems that can be adapted for use in immunological methods of the invention. One binding partner (hapten, antigen, ligand, aptamer, antibody, enzyme etc) is labelled with biotin and the other partner (surface, e.g. well, bead, sensor etc) is labelled with avidin or streptavidin. This is conventional technology for immunoassays, gene probe assays and (bio)sensors, but is an indirect immobilisation route rather than a direct one. For example a biotinylated ligand (e.g. antibody or aptamer) specific for a peptide biomarker of the invention may be immobilised on an avidin or streptavidin surface, the immobilised ligand may then be exposed to a sample containing or suspected of containing the peptide biomarker in order to detect and/or quantify a peptide biomarker of the invention. Detection and/or quantification of the immobilised antigen may then be performed by an immunological method as described herein.

The term "antibody" as used herein includes, but is not limited to: polyclonal, monoclonal, bispecific, humanised or chimeric antibodies, single chain antibodies, Fab fragments and F(ab')$_2$ fragments, fragments produced by a Fab expression library, anti-idiotypic (anti-Id) antibodies and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

The identification of key biomarkers specific to a disease is central to integration of diagnostic procedures and therapeutic regimes. Using predictive biomarkers, appropriate diagnostic tools such as biosensors can be developed, accordingly, in methods and uses of the invention, detecting and quantifying can be performed using a biosensor, microanalytical system, microengineered system, microseparation system, immunochromatography system or other suitable analytical devices. The biosensor may incorporate an immunological method for detection of the biomarker, electrical, thermal, magnetic, optical (e.g. hologram) or acoustic technologies. Using such biosensors, it is possible to detect the target biomarker at the anticipated concentrations found in biological samples.

Thus, according to a further aspect of the invention there is provided an apparatus for monitoring schizophrenia, which comprises a biosensor, microanalytical, microengineered, microseparation and/or immunochromatography system configured to detect and/or quantify the biomarker defined herein.

The biomarker of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of the biomarker of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect the biomarker of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the biomarker of the invention.

Methods involving detection and/or quantification of the peptide biomarker of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-neuromedicine.

Any suitable animal may be used as a subject non-human animal, for example a non-human primate, horse, cow, pig, goat, sheep, dog, cat, fish, rodent, e.g. guinea pig, rat or mouse; insect (e.g. *Drosophila*), amphibian (e.g. *Xenopus*) or *C. elegans*.

There is provided a method of identifying a substance capable of promoting or suppressing the generation of the peptide biomarker in a subject, comprising exposing a test cell to a test substance and monitoring the level of the peptide biomarker within said test cell, or secreted by said test cell.

The test cell could be prokaryotic, however a eukaryotic cell will suitably be employed in cell-based testing methods. Suitably, the eukaryotic cell is a yeast cell, insect cell, *Drosophila* cell, amphibian cell (e.g. from *Xenopus*), *C. elegans* cell or is a cell of human, non-human primate, equine, bovine, porcine, caprine, ovine, canine, feline, piscine, rodent or murine origin.

The test substance can be a known chemical or pharmaceutical substance, such as, but not limited to, an anti-psychotic disorder therapeutic; or the test substance can be novel synthetic or natural chemical entity, or a combination of two or more of the aforesaid substances.

In methods for identifying substances of potential therapeutic use, non-human animals or cells can be used that are capable of expressing the peptide.

Screening methods also encompass a method of identifying a ligand capable of binding to the peptide biomarker according to the invention, comprising incubating a test substance in the presence of the peptide biomarker in conditions appropriate for binding, and detecting and/or quantifying binding of the peptide to said test substance.

High-throughput screening technologies based on the biomarker, uses and methods of the invention, e.g. configured in an array format, are suitable to monitor biomarker signatures for the identification of potentially useful therapeutic compounds, e.g. ligands such as natural compounds, synthetic chemical compounds (e.g. from combinatorial libraries), peptides, monoclonal or polyclonal antibodies or fragments thereof, which may be capable of binding the biomarker.

Methods of the invention can be performed in array format, e.g. on a chip, or as a multiwell array. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g. a ligand, identified or identifiable by an identification or screening method or use of the invention. Such substances may be capable of inhibiting, directly or indirectly, the activity of the peptide biomarker, or of suppressing generation of the peptide biomarker. The term "substances" includes substances that do not directly bind the peptide biomarker and directly modulate a function, but instead indirectly modulate a function of the peptide biomarker. Ligands are also included in the term substances; ligands of the invention (e.g. a natural or synthetic chemical compound, peptide, aptamer, oligonucleotide, antibody or antibody fragment) are capable of binding, suitably specific binding, to the peptide.

The invention further provides a substance according to the invention for use in the treatment of schizophrenia, or predisposition thereto.

In one embodiment, the method additionally comprises administering an anti-psychotic drug to an individual who is diagnosed with or predicted to have schizophrenia.

Thus, according to a further aspect of the invention there is provided a method of treating a schizophrenia patient, which comprises the following steps:

(a) quantifying the amounts of the analyte biomarkers as defined herein in a biological sample obtained from an individual;

(b) comparing the amounts of the analyte biomarkers in the biological sample with the amounts present in a normal control biological sample from a normal subject, such that a difference in the level of the analyte biomarkers in the biological sample is indicative of schizophrenia, or predisposition thereto; and (c) administering an anti-psychotic drug to a patient diagnosed in step (b) as a patient with schizophrenia.

According to a further aspect of the invention, there is provided a method of treating schizophrenia in an individual in need thereof, which comprises the step of administering an anti-psychotic drug to a patient identified as having differing levels of the biomarkers as defined herein when compared to the levels of said biomarkers from a control subject.

Schizophrenia is treated primarily with anti-psychotic medications which are also referred to as neuroleptic drugs or neuroleptics. Newer anti-psychotic agents such as clozapine, olanzapine, quetiapine or risperidone are thought to be more effective in improving negative symptoms of psychotic disorders than older medication like chlorpromazine. Furthermore, they induce less extrapyramidal side effects (EPS) which are movement disorders resulting from anti-psychotic treatment.

Also provided is the use of a substance according to the invention in the treatment of schizophrenia, or predisposition thereto.

Also provided is the use of a substance according to the invention as a medicament.

Diagnostic Kits

A further aspect of the invention provides a kit for diagnosing, prognosing and/or monitoring schizophrenia comprising reagents and/or a biosensor capable of detecting and/or quantifying the biomarkers described herein. Suitably a kit according to the invention may contain one or more components selected from the group: a ligand specific for the peptide biomarker or a structural/shape mimic of the peptide biomarker, one or more controls, one or more reagents and one or more consumables; optionally together with instructions for use of the kit in accordance with any of the methods defined herein.

Diagnostic kits for the diagnosis, prognosis and monitoring of schizophrenia or other psychotic disorder are described herein. In one embodiment, the kits additionally contain a biosensor capable of detecting and/or quantifying a peptide biomarker.

The identification of biomarkers for schizophrenia or other psychotic disorder permits integration of diagnostic procedures and therapeutic regimes. Currently there are significant delays in determining effective treatment and hitherto it has not been possible to perform rapid assessment of drug response. Traditionally, many anti-psychotic therapies have required treatment trials lasting weeks to months for a given therapeutic approach. Detection of a peptide biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Therefore, future application of this test could aid clinicians in the identification of vulnerable patients early in the disease process, allowing more effective therapeutic intervention.

Biomarkers are useful in development of personalized brain therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, in a time frame and with precision, not achievable using the current subjective measures.

Furthermore, diagnostic biomarker tests are useful to identify family members or patients at high risk of developing schizophrenia or other psychotic disorder. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder, poor patient compliance or substance abuse. If pharmacological treatment is assessed to be inadequate, then therapy can be reinstated or increased; a change in therapy can be given if appropriate. As the biomarker is sensitive to the state of the disorder, it provides an indication of the impact of drug therapy or of substance abuse.

Reference Standards for Treatment

In many embodiments, the levels of one or more analyte biomarkers or the levels of a specific panel of analyte biomarkers in a sample are compared to a reference standard ("reference standard" or "reference level") in order to direct treatment decisions. The reference standard used for any embodiment disclosed herein may comprise average, mean, or median levels of the one or more analyte biomarkers or the levels of the specific panel of analyte biomarkers in a control population. The reference standard may additionally comprise cutoff values or any other statistical attribute of the control population, such as a standard deviation from the mean levels of the one or more analyte biomarkers or the levels of the specific panel of analyte biomarkers.

In some embodiments, comparing the level of the one or more analyte biomarkers is performed using a cutoff value. In related embodiments, if the level of the one or more analyte biomarkers is greater than the cutoff value, the individual may be diagnosed as having, or being at risk of developing schizophrenia. In other distinct embodiments, if the level of the one or more analyte biomarkers is less than the cutoff value, the individual may be diagnosed as having, or being at risk of developing schizophrenia. Cutoff values may be determined by statistical analysis of the control population to determine which levels represent a high likelihood that an individual does or does not belong to the control population. In some embodiments, comparing the level of the one or more analyte biomarkers is performed using other statistical methods. In related embodiments, comparing comprises logistic or linear regression. In other embodiments, comparing comprises computing an odds ratio.

In some embodiments, the control population may comprise healthy individuals or individuals with schizophrenia or prodromal syndrome.

In some embodiments, individuals with levels of one or more analyte biomarkers or levels of a specific panel of analyte biomarkers greater than the reference levels would be more likely to have schizophrenia. Therefore, an individual presenting with levels of the one or more analyte biomarkers or levels of the specific panel of analyte biomarkers greater than the reference standard would be a candidate for treatment with an anti-psychotic therapy, or with more aggressive therapy. On the other hand, an individual presenting with levels of the one or more analyte biomarkers or levels of the specific panel of analyte biomarkers less than or equal to the reference standard would be less likely to have schizophrenia and therefore be a candidate for no anti-psychotic therapy, delayed anti-psychotic therapy or less aggressive anti-psychotic therapy.

In other embodiments, individuals with levels of one or more analyte biomarkers or levels of a specific panel of analyte biomarkers less than the reference levels would be more likely to have schizophrenia. Therefore, an individual presenting with levels of the one or more analyte biomarkers or levels of the specific panel of analyte biomarkers less than the reference standard would be a candidate for treatment with anti-psychotic therapy, or with more aggressive therapy. On the other hand, an individual presenting with levels of the one or more analyte biomarkers or levels of the specific panel of analyte biomarkers greater than or equal to the reference standard would be less likely to have schizophrenia and therefore be a candidate for no anti-psychotic therapy, delayed anti-psychotic therapy or less aggressive anti-psychotic therapy.

Reference Therapy for Treatment

In some embodiments, a patient is treated more or less aggressively than a reference therapy. A reference therapy is any therapy that is the standard of care for schizophrenia. The standard of care can vary temporally and geographically, and a skilled person can easily determine the appropriate standard of care by consulting the relevant medical literature.

In some embodiments, based on a determination that levels of a panel of biomarkers is a) greater than, b) less than, c) equal to, d) greater than or equal to, or e) less than or equal to a reference standard, treatment will be either 1) more aggressive, or 2) less aggressive than a standard therapy.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Treatment of Schizophrenia

In addition to or in lieu of drug-based therapies, in some embodiments a practitioner may also treat an individual with non-drug-based anti-psychotic therapies. In some embodiments, the non-drug based therapy comprises cognitive-behavioral therapy. In some embodiments, the non-drug based therapy comprises psychotherapy. In a related embodiment, the non-drug based therapy comprises psychodynamic therapy. In some embodiments, the non-drug based therapy comprises electroconvulsive therapy. In some embodiments, the non-drug based therapy comprises hospitalization and residential treatment programs. In some embodiments, the non-drug based therapy comprises vagus nerve stimulation. In some embodiments, the non-drug based therapy comprises transcranial magnetic stimulation.

In one embodiment, the anti-psychotic treatment is selected from one or more of: chlorpromazine, haloperidol, trifluoperazine, clozapine, olanzapine, quetiapine or risperidone, in particular, clozapine, olanzapine, quetiapine or risperidone.

In one embodiment, the practitioner adjusts the anti-psychotic therapy based on a comparison between a reference level and the levels of one or more analyte biomarkers or the levels of a specific panel of analyte biomarkers in a sample from a patient. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In some embodiments, treatment comprises a less aggressive therapy than a reference therapy. In one embodiment a less aggressive therapy comprises not administering drugs and taking a "watchful waiting" approach. In one embodiment a less aggressive therapy comprises delaying treatment. In one embodiment a less aggressive therapy comprises selecting and administering less potent drugs. In one embodiment a less aggressive therapy comprises decreasing dosage of anti-psychotic drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises earlier administration of anti-psychotic drugs. In one embodiment a more aggressive therapy comprises increased dosage of anti-psychotic drugs. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based and non-drug-based therapies.

Systems for Diagnosing and Treating Schizophrenia

The results of any analyses according to the invention will often be communicated to physicians and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. The statements and visual forms can be recorded on a tangible medium such as papers, computer readable media such as hard disks, compact disks, etc., or on an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an assay is conducted outside the United States, the information and data on a test result may be generated, cast in a transmittable form as described above, and then imported into the United States. Accordingly, the present invention also encompasses a method for producing a transmittable form of information on levels of one or more analyte biomarkers or levels of a specific panel of analyte biomarkers for at least one patient sample. The method comprises the steps of (1) determining levels of one or more analyte biomarkers or levels of a specific panel of analyte biomarkers for at least one patient sample according to methods of the present invention; and (2) embodying the result of the determining step in a transmittable form. The transmittable form is the product of such a method.

Techniques for analyzing levels of one or more analyte biomarkers or levels of a specific panel of analyte biomarkers for at least one patient sample will often be implemented using hardware, software or a combination thereof in one or more computer systems or other processing systems capable of effectuating such analysis.

Thus, the present invention further provides a system for determining whether an individual suffers from schizophrenia, comprising: (1) a sample analyzer for determining the levels of one or more analyte biomarkers or levels of a specific panel of analyte biomarkers for at least one patient sample, wherein the sample analyzer contains the patient sample; (2) a first computer program for (a) receiving data regarding the levels of one or more analyte biomarkers or the levels of a specific panel of analyte biomarkers; and optionally (3) a second computer program for comparing the test value to one or more reference standards each associated with a predetermined degree of risk of schizophrenia.

The sample analyzer can be any instruments useful in determining the levels of biomarkers in a sample, as described herein.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out disease risk analysis. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instructions which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Thus one aspect of the present invention provides a system for determining whether a patient has schizophrenia. Generally speaking, the system comprises (1) computer program for receiving, storing, and/or retrieving data regarding levels of biomarkers in a patient's sample and optionally clinical parameter data (e.g., disease-related symptoms); (2) computer program for querying this patient data; (3) computer program for concluding whether an individual suffers from schizophrenia based on this patient data; and optionally (4) computer program for outputting/displaying this conclusion. In some embodiments this computer program for outputting the conclusion may comprise a computer program for informing a health care professional of the conclusion.

The practice of the present invention may also employ conventional biology methods, software and systems. Computer software products of the invention typically include computer readable media having computer-executable Instructions for performing the logic steps of the method of the invention. Suitable computer readable medium include floppy disk, CD-ROM/DVD/DVD-ROM, hard-disk drive, flash memory, ROM/RAM, magnetic tapes and etc. Basic computational biology methods are described in, for example, Setubal et al., INTRODUCTION TO COMPUTATIONAL BIOLOGY METHODS (PWS Publishing Company, Boston, 1997); Salzberg et al. (Ed.), COMPUTATIONAL METHODS IN MOLECULAR BIOLOGY, (Elsevier, Amsterdam, 1998); Rashidi & Buehler, BIOINFORMATICS BASICS: APPLICATION IN BIOLOGICAL SCIENCE AND MEDICINE (CRC Press, London, 2000); and Ouelette & Bzevanis, Attorney Docket No. 3330-01-1P Page 38 of 64 BIOINFORMATICS: A PRACTICAL GUIDE FOR ANALYSIS OF GENE AND PROTEINS (Wiley & Sons, Inc., 2nd ed., 2001); see also, U.S. Pat. No. 6,420,108.

patient groups for age, gender and social demographics. Controls with first degree relatives with a history of mental disease or other medical conditions such as type 2 diabetes, cardiovascular or autoimmune diseases were not included in the study. Schizophrenia patients with medical co-morbidities were also excluded. Apart from anti-psychotic use, data of medication use prior to hospitalization was not available. Psychiatric medication was administered after completion of diagnostic evaluation as appropriate.

TABLE 1

Patient and control baseline characteristics

| | Number | Centre | M/F | Age (years) | BMI (kg/m$^2$) | Smoking (Y\|N\|NR) | Cannabis (Y\|N\|NR) | PANSS pos | PANSS neg | PANSS gen | CAARMS pos |
|---|---|---|---|---|---|---|---|---|---|---|---|
| Cohort 1 | 52 CT | Mannheim | 27/25 | 30 ± 8 | 23 ± 3 | 20\|32\|0 | 30\|21\|1 | NA | NA | NA | NA |
| (106) | 54 SCZ | | 32/22 | 30 ± 10 | 23 ± 4 | 23\|21\|0 | 31\|20\|3 | 23 ± 5 | 24 ± 8 | 49 ± 10 | NA |
| Cohort 2 | 73 CT | Magdeburg | 46/27 | 32 ± 9 | 25 ± 4 | 20\|53\|0 | 2\|56\|15 | NA | NA | NA | NA |
| (106) | 33 SCZ | | 22/11 | 31 ± 10 | 24 ± 4 | 24\|9\|0 | 9\|24\|0 | 21 ± 6 | 19 ± 9 | 43 ± 12 | NA |
| Cohort 3 | 23 CT | Magdeburg | 10/13 | 33 ± 11 | 23 ± 3 | 5\|18\|0 | 0\|23\|0 | NA | NA | NA | NA |
| (39) | 16 SCZ | | 8/8 | 35 ± 11 | 21 ± 2 | 6\|9\|1 | 0\|15\|1 | 19 ± 8 | 16 ± 4 | 37 ± 12 | NA |
| Cohort 4 | 16 CT | Magdeburg | 8/8 | 35 ± 11 | 23 ± 3 | 1\|15\|0 | 0\|16\|0 | NA | NA | NA | NA |
| (26) | 10 SCZ | | 6/4 | 37 ± 12 | 22 ± 3 | 5\|5\|0 | 0\|10\|0 | 19 ± 8 | 14 ± 8 | 33 ± 21 | NA |
| Cohort 5 | 40 CT | Erasmus | 33/7 | 26 ± 4 | NR | NR | NR | NA | NA | NA | NA |
| (54) | 14 SCZ | | 11/3 | 24 ± 6 | NR | 10\|4\|0 | 8\|6\|0 | 21 ± 3 | 19 ± 4 | 35 ± 8 | NA |
| Cohort 6 | 88 CT | Santander | 51/37 | 33 ± 8 | 26 ± 4 | 51\|37\|0 | 22\|66\|0 | NA | NA | NA | NA |
| (135) | 47 SCZ | | 28/19 | 30 ± 9 | 23 ± 5 | 24\|23\|0 | 20\|27\|0 | 24 ± 3* | 13 ± 6* | NR | NA |
| Cohort 7 (46) | 46 SCZ | Muenster | 35/11 | 27 ± 9 | NR | NR | NR | 18 ± 7 | 18 ± 7 | NR | NA |
| USA military (369) | 184 CT | USA DoDSR | 136/48 | 22 ± 4 | NR | NR | NR | NA | NA | NA | NA |
| | 75 pre-SCZ | | 67/8 | 24 ± 5 | NR | NR | NR | NR | NR | NR | NA |
| | 110 pre-BD | | 70/40 | 21 ± 4 | NR | NR | NR | NR | NR | NR | NA |
| Prodromal/ | 18 pre-SCZ | Paris | 11/7 | 20 ± 3 | 21 ± 3 | 9\|8\|1 | 7\|11\|0 | 16 ± 7 | 17 ± 7 | 41 ± 11 | 13 ± 7 |
| help-seeker (72) | 58 Not pre-SCZ | | 33/25 | 22 ± 4 | 22 ± 4 | 26\|24\|8 | 12\|46\|0 | 12 ± 5 | 15 ± 7 | 38 ± 10 | 8 ± 6 |

Legend:
M/F = male/female;
BMI = body mass index;
PANSS = positive and negative syndrome scale;
Y = yes;
N = no;
NR = not recorded;
NA = not applicable;
pos = positive;
neg = negative;
gen = general;
values were obtained via conversion of SAPS and SANS scores (van Erp T. G. et al. (2014) *Schizophr. Res.* 152(1): 289-94).
CAARMS = Comprehensive Assessment of At-Risk Mental State.
Values are presented as average ± standard deviation.

The following studies illustrate the invention.
Methods
Clinical Cohorts

For the discovery phase of the study, individuals were recruited from two clinical centres in Germany (cohort 1, Central Institute of Mental Health, Mannheim; cohorts 2-4, University of Magdeburg) and one in the Netherlands (cohort 5, Erasmus University MC, Rotterdam). All patients in cohorts 1-5 were diagnosed as having the paranoid subtype of schizophrenia (295.30). For the validation phase, subjects were recruited from clinics in Germany (cohort 6, University of Muenster) and Spain (cohort 7, University of Cantabria) (Table 1). DSM-IV diagnosis was performed by psychiatrists and additional analysis included Positive and Negative Syndrome Scale (PANSS) testing (Institute AP. Diagnostic and statistical manual of mental disorders DSM-IV-TR. 4th ed. Arlington, Va.: American Psychiatric Association; 2000). Patients were first- or recent-onset and antipsychotic-naive at the time of sample collection. Controls were recruited from the same institutions and matched the respective For the test phase, cohort 8 samples were selected from the USA Department of Defense Serum Repository (DoDSR; excess serum remaining from mandatory HIV testing of military personnel) comprising two nested case-control studies of personnel who retired from the military with a DSM-IV diagnosis of schizophrenia (295.10-295.30, 295.60, 295.70, 295.90) or bipolar disorder (296.00-296.06, 296.40-296.7, 296.80, 296.89) (Military New Onset Psychosis Project), as described previously (Table 1) (Li Y. et al. (2013) *Schizophr. Res.* 151(1-3):36-42; Millikan A. M. et al. (2007) *Mil. Med.* 172(10):1032-8; Schwarz E. et al. (2012) *World J. Biol. Psychiatry* 13(8):627-32). Sera had been collected approximately 30 days before onset of the first psychiatric symptoms and transferred to the Johns Hopkins School of Medicine prior to testing. Sample retrieval was performed by the Armed Forces Health Surveillance Centre and coordinated by the Walter Reed Army Institute of Research. Cohort 9 consisted of 76 individuals who were enrolled in the ICAAR collaborative study and investigated at the Adolescent and Young Adults Assessment Centre (SHU, Paris) between 2009 and 2011. Inclusion criteria required alteration in global functioning (GAF<70) during the last year associated with psychological distress and/or decline in functioning and/or psychiatric symptoms. Subjects with manifest symptoms of psychosis (fulfilling DSM-IV criteria for schizophrenia or schizo-affective disorders), pervasive developmental or bipolar disorders were excluded, as were individuals with other established diagnoses such as obsessive-compulsive disorder. Other exclusion criteria were: current antipsychotic treatment for more than 12 weeks; psychoactive substance dependence or abuse during the previous year and/or greater than 5 years; serious or evolutive somatic and neurological disorders; head injury and IQ lower than 70; and non-French-native speaking. The Comprehensive Assessment of At-Risk Mental State (CAARMS) was conducted by specifically trained psychiatrists (Magaud E. et al. (2014) *Schizophr. Res.* 152(2-3):415-20). Among the 76 prodromal help-seekers, 50 met the CAARMS threshold criteria for ultra-high risk and 26 did not (Magaud E. et al. (2010) *Schizophr. Res.* 123(1):53-8). Of the 50 individuals who met the CAARMS criteria, 14 later developed schizophrenia and 36 did not. Of the 26 individuals who did not meet the CAARMS criteria, 4 developed schizophrenia and 22 did not. This resulted in a total of 18 prodromal/non-prodromal help-seekers who later developed schizophrenia and 58 who did not.

Informed written consent was given by all participants other than those from the USA military cohort (a consent waiver was obtained as the study comprised blinded data and involved no contact with the subjects). All study protocols, analysis of samples and test methods were approved by the local Institutional Review Boards and were in compliance with the Standards for Reporting of Diagnostic Accuracy (Bossuyt P. M. et al. (2003) *Croat. Med. J.* 44(5):635-8).

Multiplexed Immunoassay Analyses

The Multi-Analyte Profiling immunoassay platform was used to measure the concentrations of 150-250 analytes in serum samples prepared according to standard procedures at the respective institutions. All assays were conducted in the Clinical Laboratory Improved Amendments (CLIA)-certified laboratory at Myriad-RBM, as described (Schwarz E. et al. (2012) *Mol. Psychiatry* 17(5):494-502).

Statistical Analysis

All statistical analyses were performed in R (http://www.R-project.org/). Multiplex immunoassay data were pre-processed to remove analytes with greater than 30% missing values. Sample outliers were identified using the first four principal components (Barnett V. and Lewis T. Outliers in Statistical Data. New York: John Wiley & Sons, Inc.; 1978), resulting in removal of one control from the USA military cohort. Data were imputed as described previously (Schwarz E. et al. (2012) *Mol. Psychiatry* 17(5):494-502) and log 10-transformed to stabilize variance. For meta-analysis of cohorts 1-5, batch effects were eliminated using ComBat in the sva package (Johnson W. E. et al. (2007) *Biostatistics* 8(1):118-27). Eighty-nine analytes passed quality control and were tested for association with patient/control status using logistic regression (age and sex were not associated). Model assumptions for the associated analytes were also tested. False discovery rate was controlled according to Benjamini and Hochberg. Sixty-two analytes remained after excluding those with significant association heterogeneity, resulting in $2^{62}=4.61\times10^{18}$ possible candidate models. To reduce the model space, only the analytes associated with patient/control status were used (P<0.05; no correction for multiple testing) and lasso regression as implemented in the R package glmnet (Hastie T. et al. The Elements of Statistical Learning: Data Mining, Inference, and Prediction. 5th ed. New York: Springer; 2001; Tibshirani R. (1996) *J. Royal Statist. Soc. B.*). Lasso is a penalized method for restricting the residual sum of squares and constraining the sum of the absolute values of the coefficients: $\Sigma_i|\beta_i|\leq t$, where t is the 'tuning' parameter. As $t\to\infty$, t has no effect and the solutions are the least squares estimates for the full model. For smaller t values, solutions are shrunken versions of the least squares estimates with many coefficients decreased to the null value. t was defined using ten-fold cross-validation. The details of subject inclusion and marker selection are summarised in FIG. 1.

Performance of the biomarker panel was evaluated in independent cohorts using accuracy, sensitivity, specificity, predictive values, likelihood ratios, receiver operating characteristic (ROC) curves and area under the ROC curve (AUC: 0.9-1=excellent; 0.8-0.9=good; 0.7-0.8=fair; 0.6-0.7=poor; 0.5-0.6=fail). Optimal trade-offs between sensitivity and specificity were determined by maximising the Youden's index (J; calculated by J=sensitivity+specificity−1) (Fluss R. et al. (2005) *Biom. J.* 47(4):458-72).

Results

The study included 957 participants, comprised of 331 in the discovery cohort, 181 in the two validation cohorts, 369 in the USA military cohort and 76 in the prodromal/help-seeker cohort (Table 1, FIG. 1). The comparative groups within each cohort were matched for age and sex, and those in the USA military and prodromal/help-seeker cohorts were approximately 10 years younger compared to those in the discovery and validation cohorts.

Stage I. Discovery of a First-Onset (FO) Schizophrenia Biomarker Panel

Figure 2:
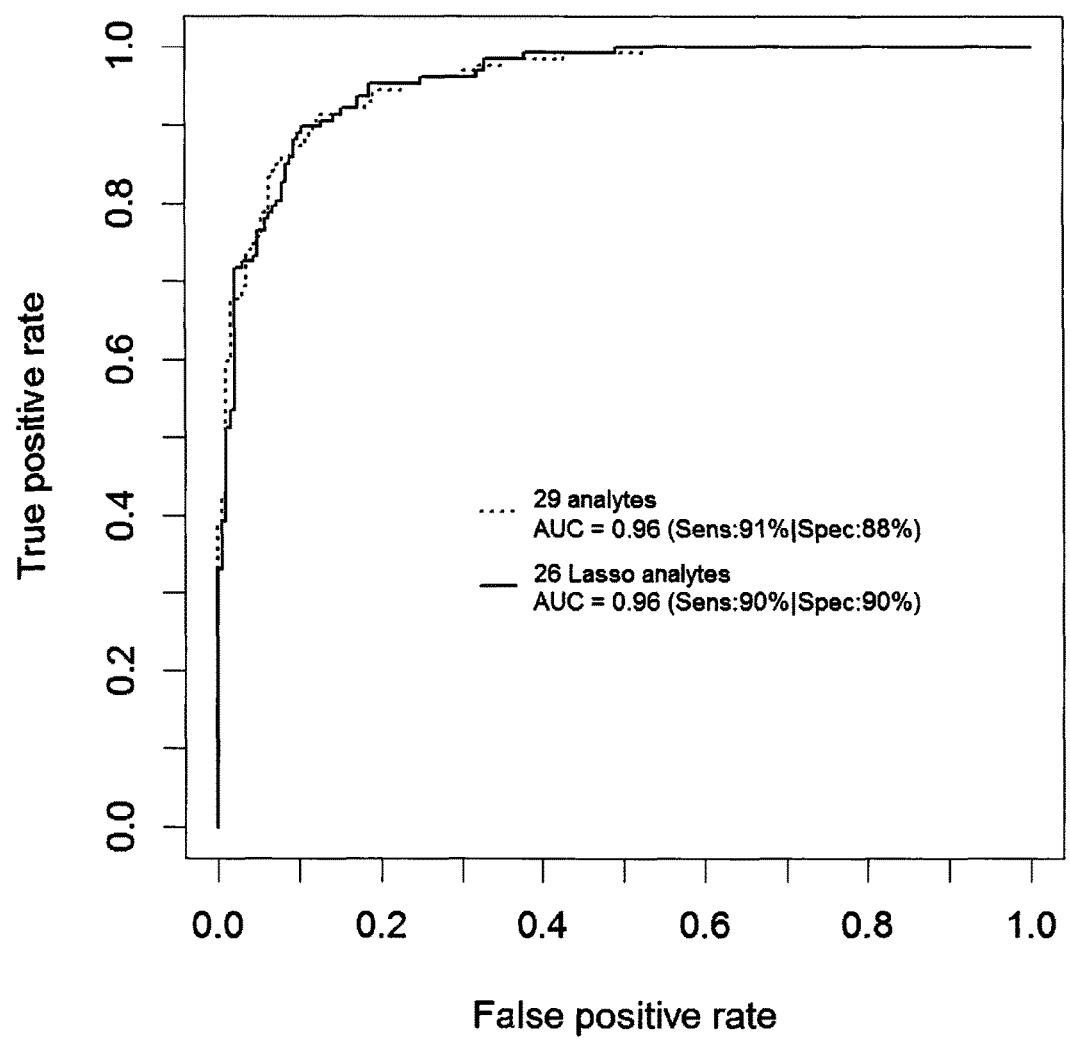
FIG. 2: ROC curves showing the diagnostic performance achieved using the 29 original analyte combination and the 26 final Lasso selected SCZ analyte panel in discriminating SCZ patients from controls (discovery cohort, 127 SCZ and 204 controls). SCZ=schizophrenia; ROC=receiver operator characteristic; AUC=area under curve; Sens=sensitivity; Spec=specificity

Meta-analysis of cohorts 1-5 identified 29 out of 62 analytes altered in schizophrenia patients compared to controls (Table 2). Lasso regression with 10-fold cross-validation was used to select an optimal set of 26 analytes for the first onset schizophrenia biomarker panel (Table 2). The performance using the 26 analyte panel (AUC=0.96, sensitivity=90%, specificity=90%) was similar to that achieved using the 29 analytes (AUC=0.96, sensitivity=91%, specificity=88%; FIG. 2). The sensitivity and specificity values reported were selected based on the highest Youden's index (J) obtained for each cut-off value. The 26 analytes were involved in six main molecular functions: lipid transport (ApoA1, ApoH); inflammation (A2M, B2M, CA, HAPT, IL1ra, IL8, IL10, IL13, MIF, RAGE, SGOT, TNC, vWF); immune system (IgA); hormonal signaling (FSH, leptin, PPP, TEST, TSH); growth factor signaling (AXL, IGFBP2, SCF); and the clotting cascade (ACE, FVII) (see Table 2 for complete analyte names).

TABLE 2

Marker selection: analytes altered in patients compared to controls.

| Molecular Function | Analyte | Abbrev | Lasso selected | Coefficient | Std. Error | P-value | Adjusted P-value |
|---|---|---|---|---|---|---|---|
| Lipid transport | Apolipoprotein H | ApoH | ✓ | 2.67 | 1.05 | 0.011 | 0.032 |
| | Apolipoprotein A1 | ApoAI | ✓ | −1.48 | 0.66 | 0.026 | 0.062 |
| Inflammatory response | Macrophage migration inhibitory factor | MIF | ✓ | 2.89 | 0.48 | 1.75E−09 | 1.56E−07 |
| | Carcinoembryonic antigen | CA | ✓ | 1.77 | 0.36 | 1.13E−06 | 1.68E−05 |
| | Tenascin C | TNC | ✓ | 2.89 | 0.62 | 3.57E−06 | 3.97E−05 |
| | Interleukin-10 | IL10 | ✓ | 3.55 | 0.83 | 1.70E−05 | 1.51E−04 |
| | Interleukin-1 receptor antagonist | IL1ra | ✓ | 1.83 | 0.46 | 6.27E−05 | 4.30E−04 |
| | Receptor for advanced glycosylation end products | RAGE | ✓ | −2.01 | 0.52 | 1.10E−04 | 7.00E−04 |
| | Interleukin-8 | IL8 | ✓ | 2.30 | 0.62 | 2.12E−04 | 1.25E−03 |
| | Haptoglobin | HAPT | ✓ | 1.38 | 0.37 | 2.30E−04 | 1.25E−03 |
| | von Willebrand factor | VWF | ✓ | 1.69 | 0.56 | 0.003 | 0.010 |
| | Alpha-2 macroglobulin | A2M | ✓ | 3.22 | 1.07 | 0.003 | 0.010 |
| | Beta-2 microglobulin | B2M | ✓ | −4.04 | 1.55 | 0.009 | 0.029 |
| | Serum glutamic oxaloacetic transaminase | SGOT | ✓ | 1.90 | 0.83 | 0.022 | 0.055 |
| | Interleukin-13 | IL13 | ✓ | 1.32 | 0.67 | 0.050 | 0.103 |
| Immune system | Immunoglobulin A | IgA | ✓ | −1.54 | 0.63 | 0.015 | 0.042 |
| Hormonal signalling | Pancreatic polypeptide | PPP | ✓ | 1.97 | 0.34 | 4.12E−09 | 1.83E−07 |
| | Leptin | Leptin | ✓ | −1.55 | 0.28 | 5.42E−08 | 1.21E−06 |
| | Testosterone (Total) | TEST | ✓ | 2.08 | 0.59 | 4.11E−04 | 0.002 |
| | Follicle-stimulating hormone | FSH | ✓ | 1.17 | 0.34 | 5.19E−04 | 0.002 |
| | Thyroid stimulating hormone | TSH | ✓ | −1.19 | 0.50 | 0.017 | 0.047 |
| Growth Factor signalling | Insulin-like growth factor-binding protein 2 | IGFBP2 | ✓ | 2.96 | 0.62 | 1.97E−06 | 2.51E−05 |
| | AXL receptor tyrosine kinase | AXL | ✓ | −2.35 | 0.82 | 0.004 | 0.014 |
| | Stem Cell Factor | SCF | ✓ | −2.20 | 0.87 | 0.011 | 0.032 |
| Clotting cascade | Factor VII | FVII | ✓ | −3.92 | 0.87 | 6.50E−06 | 6.43E−05 |
| | Angiotensin-converting enzyme | ACE | ✓ | −1.39 | 0.67 | 0.037 | 0.082 |
| Hormonal signalling | Chromogranin-A * | CGA | — | 0.54 | 0.24 | 0.024 | 0.060 |
| Growth Factor signalling | Vascular cell adhesion molecule-1 * | VCAM1 | — | −2.63 | 1.25 | 0.036 | 0.082 |
| Inflammatory response | Eotaxin * | Eotaxin | — | 0.98 | 0.48 | 0.041 | 0.087 |

The analytes are ranked in order of significance within each molecular function group.
Std. Error = standard error,
Abbrev = abbreviation;
* not selected by Lasso.

Stage II. Validation of the Biomarker Panel

Figure 3:
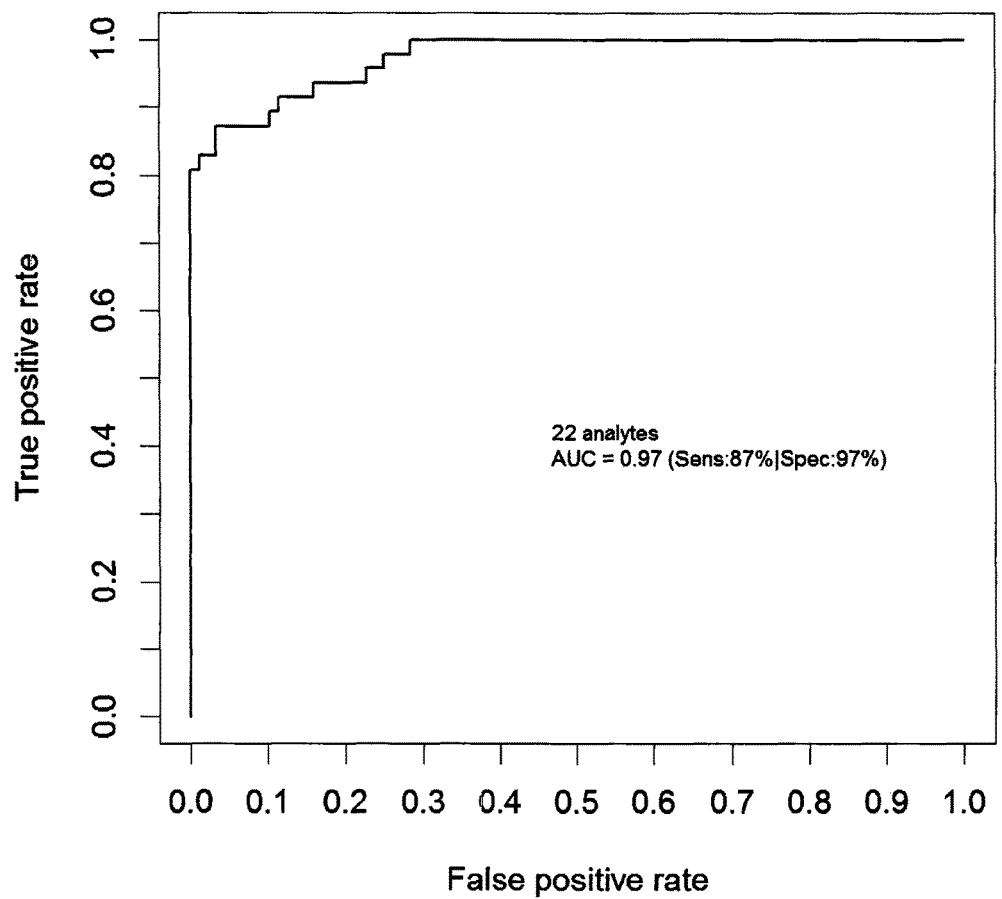
FIG. 3: ROC curve analysis showing the diagnostic performance achieved using the analyte panel for discriminating first or recent onset SCZ patients from controls (validation cohort 6, 47 SCZ and 88 controls). SCZ=schizophrenia; AUC=area under the curve; Sens=sensitivity; Spec=specificity.

Diagnostic performance of the 26 analyte panel was assessed using two independent schizophrenia patient cohorts (cohorts 6 and 7). As four analytes were excluded (CA, IL10, IL13, SGOT; >30% missing values) for cohort 6, a reduced panel of 22 analytes was tested, which yielded an AUC of 0.97 (sensitivity=87%, specificity=97%, PPV=93%, NPV=93%, accuracy=93%, LRP=29.0, LRN=0.1) (Table 3; FIG. 3). The full panel was tested on cohort 7, which consisted of schizophrenia patients only. Two classification algorithms, logistic regression and linear discriminant analysis, were trained on the discovery cohort and tested on cohort 7, resulting in correct classification (sensitivity) of 89% (Table 3).

Stage III. Predictive Performance Testing of the Biomarker Panel

Figure 4:
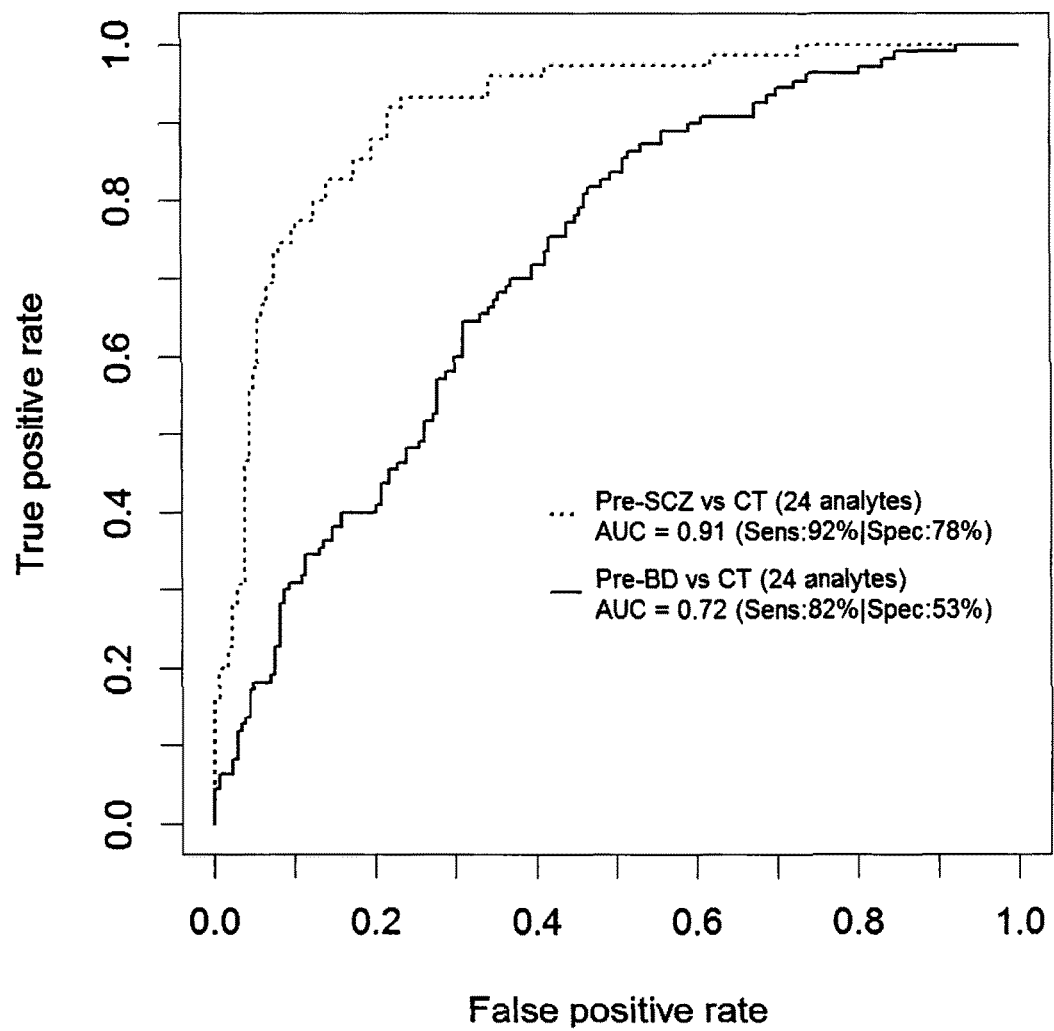
FIG. 4: ROC curve analysis showing diagnostic performance of the SCZ analyte panel in discriminating subjects who later developed schizophrenia (n=75) or bipolar disorder (n=110) from controls (n=184) (USA military cohort). SCZ=schizophrenia; BD=bipolar disorder; CT=control; AUC=area under the curve; Sens=sensitivity; Spec=specificity.

The predictive performance of the panel was tested on the pre-schizophrenia (USA military) and prodromal/help-seeker cohorts. In the military cohort, two analytes were excluded (A2M, IL10; >30% missing values) and a reduced panel of 24 analytes was tested. This gave an AUC of 0.91 for predicting development of schizophrenia in personnel who were sampled 30 days or more prior to manifestation of symptoms (sensitivity=92%, specificity=78%, PPV=63%, NPV=96%, accuracy=82%, LRP=4.2, LRN=0.1). Specificity of the panel was evaluated by testing on samples from military personnel who later developed bipolar disorder. This resulted in a lower test performance with an AUC of 0.72 (sensitivity=82%, specificity=53%, PPV=51%, NPV=83%, accuracy=64%, LRP=1.7, LRN=0.3) (Table 3; FIG. 4).

TABLE 3

Assay Performance.

| | AUC (95% CI) | FP | TP | TN | FN | PPV (%) | NPV (%) | Sens (%) | Spec (%) | FPR (%) | Acc (%) | LRP | LRN |
|---|---|---|---|---|---|---|---|---|---|---|---|---|---|
| | Discovery cohort (schizophrenia compared to controls) | | | | | | | | | | | | |
| 29 analyte panel | 0.96 (0.938-0.977) | 25 | 116 | 179 | 11 | 82 | 94 | 91 | 88 | 12 | 89 | 7.6 | 0.1 |
| 26 Lasso panel | 0.96 (0.937-0.976) | 21 | 114 | 183 | 13 | 84 | 93 | 90 | 90 | 10 | 90 | 9.0 | 0.1 |
| | Validation cohorts (schizophrenia compared to controls) | | | | | | | | | | | | |
| Cohort 6 | 0.97 (0.952-0.996) | 3 | 41 | 85 | 6 | 93 | 93 | 87 | 97 | 3 | 93 | 29.0 | 0.1 |
| Cohort 7 (only SCZ)[#][*] | NA | NA | 41 | NA | 5 | NA | NA | 89 | NA | NA | NA | NA | NA |
| | USA military (pre-schizophrenia/pre-bipolar disorder compared to controls) | | | | | | | | | | | | |
| Pre-SCZ | 0.91 (0.870-0.949) | 40 | 69 | 144 | 6 | 63 | 96 | 92 | 78 | 22 | 82 | 4.2 | 0.1 |
| Pre-BD | 0.72 (0.663-0.779) | 86 | 90 | 98 | 20 | 51 | 83 | 82 | 53 | 47 | 64 | 1.7 | 0.3 |
| | Prodromal/help-seeker cohort (individuals who later developed SCZ compared to those who did not) | | | | | | | | | | | | |
| 22 analyte panel | 0.82 (0.706-0.925) | 20 | 16 | 38 | 2 | 44 | 95 | 89 | 66 | 34 | 71 | 2.6 | 0.2 |
| 22 analyte panel + CAARMS positive | 0.90 (0.816-0.978) | 12 | 16 | 46 | 2 | 57 | 96 | 89 | 79 | 21 | 82 | 4.2 | 0.1 |
| CAARMS positive | 0.72 (0.568-0.865) | 23 | 14 | 35 | 4 | 38 | 90 | 78 | 60 | 40 | 64 | 2.0 | 0.4 |

Classification algorithm:
[#]logistic regression and
[*]linear discriminant analysis (identical results);
AUC = area under curve;
PPV = positive predictive value;
NPV = negative predictive value;
FPR = false positive rate;
FP = number of false positives;
TP = number of true positives;
TN = number of true negatives;
FN = number of false negatives;
CAARMS = Comprehensive Assessment of At-Risk Mental State;
LRP = Positive likelihood ratio;
LRN = Negative likelihood ratio;
Sens = sensitivity;
Spec = specificity.

Figure 5:
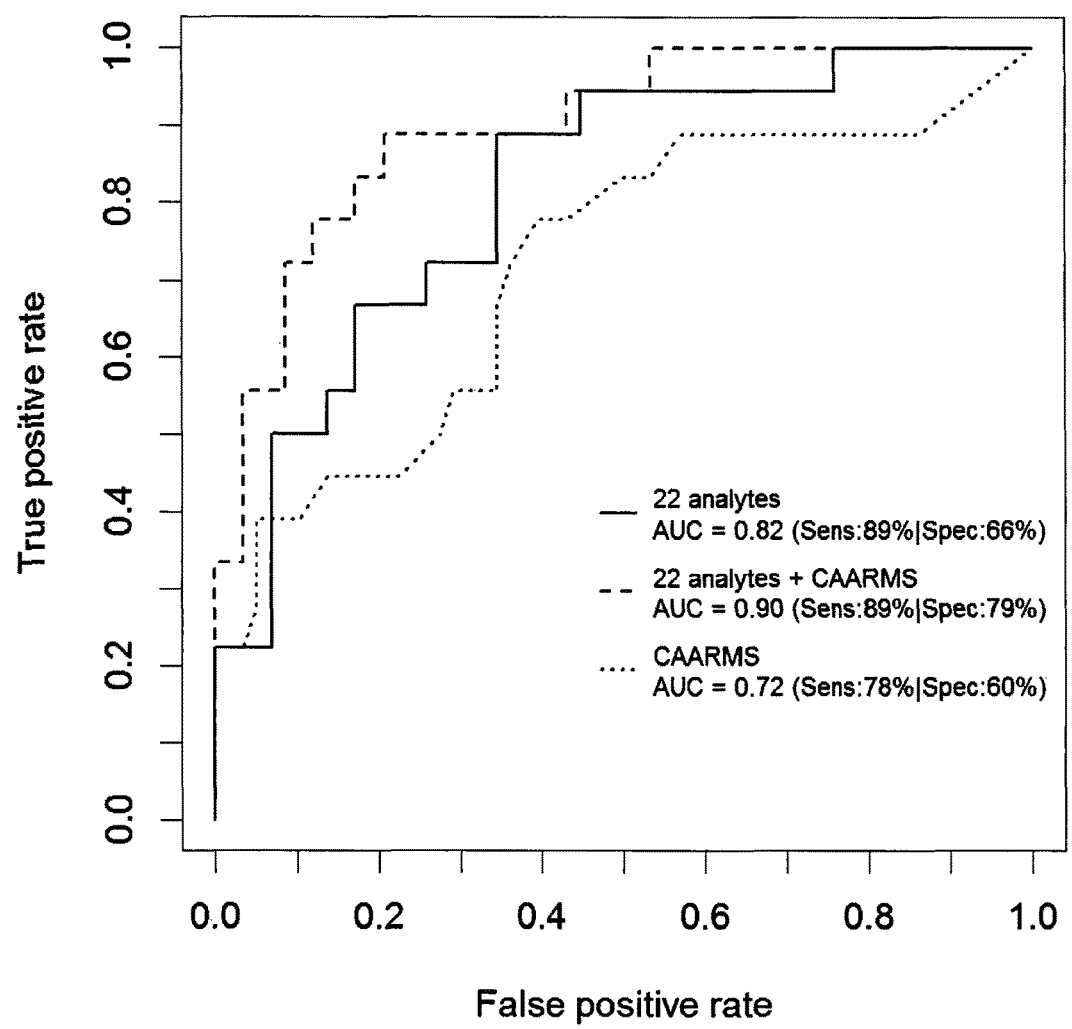
FIG. 5: ROC curve analysis showing diagnostic performance of the SCZ analyte panel for discrimination of subjects who later developed schizophrenia (18) from those who did not (58) (prodromal/help-seeker cohort). AUC=area under the curve; CAARMS=Comprehensive Assessment of At-Risk Mental State.
Figure 6:
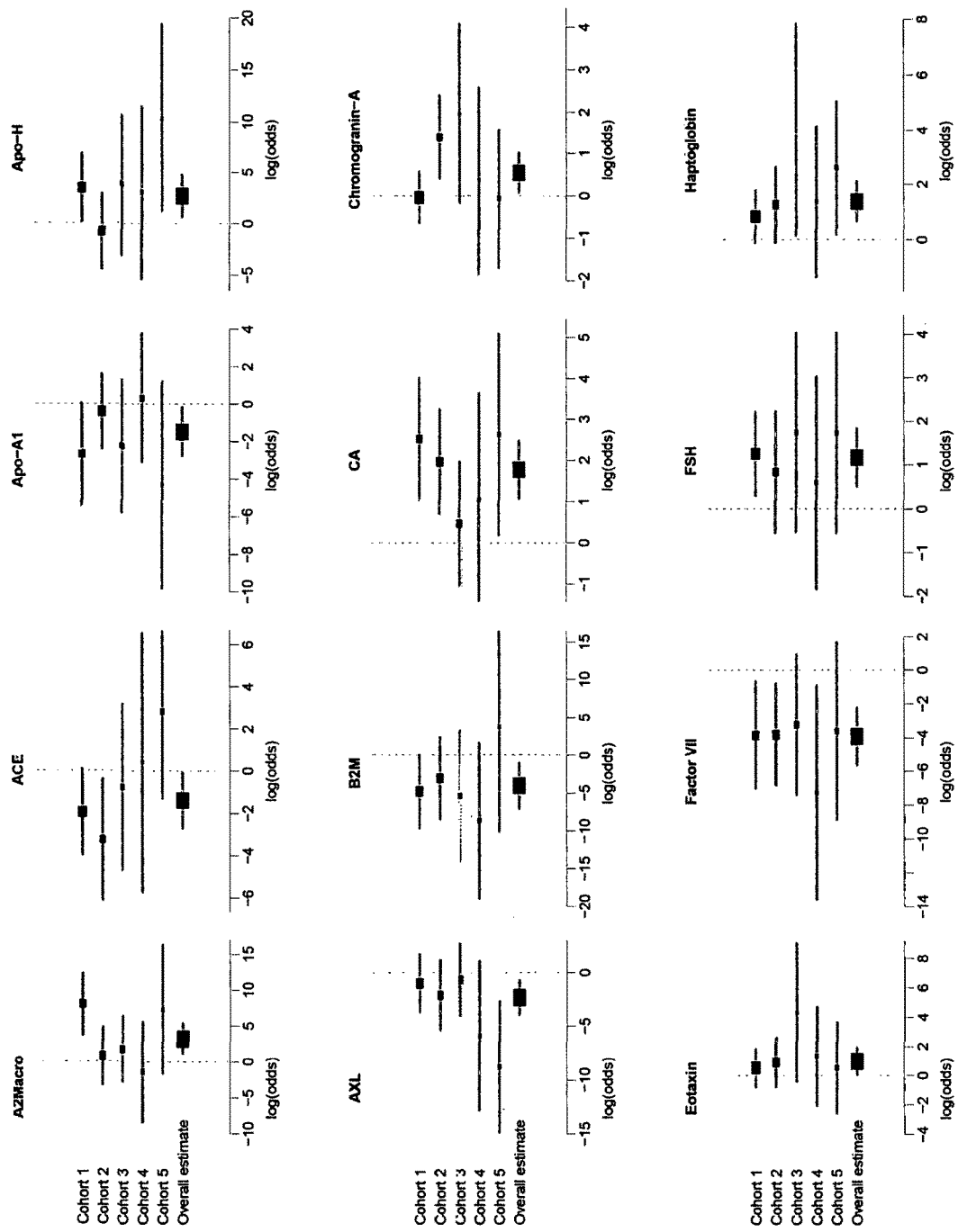
FIG. 6: Forest plots of overall effect size (estimate) for the 29 analytes associated with the SCZ patient/control status by cohort. Overall effect size was estimated using meta-analysis (cohorts 1-5 combined). The black squares represent the effect estimates for the individual cohorts, and the horizontal lines represent the 95% confidence intervals (CIs) of the estimates. The sizes of the squares are proportional to the weights of the estimates. Note that the data have been log 10 transformed and had batch effects removed (see Methods section).

In the prodromal/help-seeker cohort, four analytes were excluded (CA, IL10, IL13, SGOT; >30% missing values), resulting in a reduced 22-analyte panel being tested (same panel tested on cohort 6), which resulted in an AUC of 0.82 (sensitivity=89%, specificity=66%, PPV=44%, NPV=95%, accuracy=71%, LRP=2.6, LRN=0.2). Diagnostic performance was improved by incorporation of CAARMS positive subscale scores into the model (AUC=0.90, sensitivity=89%, specificity=79%, PPV=57%, NPV=96%, accuracy=82%, LRP=4.2, LRN=0.1). The predictive performance of the CAARMS positive subscale scores alone was lower (AUC=0.72, sensitivity=78%, specificity=60%, PPV=38%, NPV=90%, accuracy=64%, LRP=2.0, LRN=0.4) (Table 3; FIG. 5).

Further Results

Analyte combinations were then selected further based on joint effects (Table 4 and 5).

TABLE 4

Model selection - optimal analyte panel testing (Lasso regression applied).

| 21 analytes | Model1 | Model2 | Model3 | Model4 | Model5 | Model6 | Model7 |
|---|---|---|---|---|---|---|---|
| ACE | 0.00 | 0.00 | 0.00 | 0.00 | 0.00 | yes | yes |
| ApoAI | 0.00 | 0.00 | 0.00 | 0.00 | 0.00 | 0.00 | yes |
| ApoH | 0.00 | 0.00 | 0.00 | 0.00 | 0.00 | yes | yes |
| AXL | 0.00 | 0.00 | 0.00 | yes | yes | yes | yes |
| B2M | 0.00 | 0.00 | 0.00 | 0.00 | yes | yes | yes |
| FactorVII | 0.00 | 0.00 | yes | yes | yes | yes | yes |
| FSH | 0.00 | 0.00 | 0.00 | yes | yes | yes | yes |
| Haptoglobin | 0.00 | 0.00 | yes | yes | yes | yes | yes |
| IgA | 0.00 | 0.00 | 0.00 | 0.00 | 0.00 | yes | yes |
| IGFBP2 | 0.00 | 0.00 | 0.00 | yes | yes | yes | yes |
| IL1ra | 0.00 | 0.00 | 0.00 | yes | yes | yes | yes |
| IL8 | 0.00 | 0.00 | 0.00 | 0.00 | yes | yes | yes |
| Leptin | 0.00 | yes | yes | yes | yes | yes | yes |
| MIF | yes | yes | yes | yes | yes | yes | yes |
| PPP | yes | yes | yes | yes | yes | yes | yes |
| RAGE | 0.00 | 0.00 | yes | yes | yes | yes | yes |
| SCF | 0.00 | 0.00 | 0.00 | 0.00 | yes | yes | yes |
| Testosterone (Total) | 0.00 | 0.00 | 0.00 | 0.00 | 0.00 | 0.00 | yes |

TABLE 4-continued

Model selection - optimal analyte panel testing (Lasso regression applied).

| 21 analytes | Model1 | Model2 | Model3 | Model4 | Model5 | Model6 | Model7 |
|---|---|---|---|---|---|---|---|
| TNC | 0.00 | 0.00 | yes | yes | yes | yes | yes |
| TSH | 0.00 | 0.00 | 0.00 | 0.00 | 0.00 | 0.00 | 0.00 |
| VWF | 0.00 | 0.00 | 0.00 | 0.00 | yes | yes | yes |
| Number of analytes selected | 2 | 3 | 7 | 11 | 15 | 18 | 20 |

TABLE 5

AUCs obtained using the analyte panels identified by each model.

| Analytes | Discovery cohort | Santander | Military | Prodromal |
|---|---|---|---|---|
| 2 | 0.79 | 0.71 | 0.62 | 0.56 |
| 3 | 0.81 | 0.75 | 0.71 | 0.55 |
| 7 | 0.89 | 0.90 | 0.75 | 0.67 |
| 11 | 0.90 | 0.93 | 0.78 | 0.69 |
| 15 | 0.92 | 0.94 | 0.81 | 0.70 |
| 18 | 0.92 | 0.96 | 0.83 | 0.77 |
| 20 | 0.93 | 0.97 | 0.90 | 0.77 |
| 21 | 0.93 | 0.97 | 0.90 | 0.80 |

The 21 analyte panel can be used to accurately discriminate schizophrenia patients from controls as well as help-seeker prodromal converters from non-converters (AUC=0.80). Any panel including less than 21 analytes achieves fair performance with AUC<0.77 for discriminating help-seeker prodromal converters from non-converters.

Discussion

This study has identified a serum molecular biomarker panel for identification of individuals with schizophrenia using a stringent meta-analysis of five cohorts of first-onset antipsychotic-naïve patients. These findings were validated by showing that the panel yielded excellent diagnostic performance when applied to individuals from two independent first/recent onset schizophrenia patient cohorts. Importantly, the primary objective was achieved by showing that the panel had good prognostic/predictive accuracy (AUC=0.82) for identification of patients who later converted from prodromal syndrome to schizophrenia. In addition, the secondary objective was achieved by showing that the panel had excellent performance (AUC=0.91) for identification of individuals who did not display overt psychopathology at the time of sample collection and later developed schizophrenia. In contrast, lower performance was achieved (AUC=0.72) when the same panel was used to test samples from individuals who were later diagnosed with bipolar disorder, demonstrating good specificity of the panel for schizophrenia.

For all predictions, we identified optimal cut-offs based on the best trade-off between the highest sensitivity and specificity. This resulted in a high proportion of correctly predicted prodromal converters (89%) and pre-symptomatic individuals (92%) who later developed schizophrenia, as well as true negative individuals comprising those who did not develop the illness (66%) and controls (78%). Identification of these individuals is of particular importance to avoid unnecessary exposure to potential risks and side-effects of therapy and medication. Therefore, further developments of this biomarker panel could lead to implementation of a clinical test for early and accurate risk estimation (Ruhrmann S. et al. (2012) *Eur. Arch. Psychiatry Clin. Neurosci.* 262 Suppl 2:S85-90). It should be noted that sensitivity and specificity are generally constant properties of a test, while Positive Predictive Value (PPV) and Negative Predictive Value (NPV) give the risk estimation, which is clinically useful. However, PPV and NPV are prevalence-dependent measures and therefore performance can vary in different settings (Hennekens C. H. and Buring J. E. Epidemiology in medicine: New York: Little Brown; 1987). This is why even excellent tests have a poor PPV when the disease has low prevalence in the test population. For clinical applications, the use of Youden's index may not be the most appropriate option to select optimal cut-off values. Instead, selections maximizing sensitivity, specificity and diagnostic test accuracy should be made based on clinical need.

Recently, studies evaluating magnetic resonance imaging-based tests or psychopathological symptoms have shown high diagnostic accuracy (75-92%) (for review, see Zarogianni E. et al. (2013) *Neuroimage Clin.* 3:279-89) in discriminating schizophrenia or pre-schizophrenia patients from controls. However, most of these studies have sample size limitations. Classification models based on small sample sizes tend to favour diagnostic performance. Though validation using larger sample sets is still needed, the current findings are encouraging. Further study of the schizophrenia biomarker candidates identified here could also lead to new insights into schizophrenia pathophysiology. Most of the analytes used in the final panel are involved in the inflammation response or hormonal and growth factor pathways, consistent with the findings of previous studies (Schwarz E. et al. (2012) *Mol. Psychiatry.* 17(5):494-502; Schwarz E. et al. (2013) *Schizophr. Bull.*; Domenici E. et al. (2010) *PLoS One* 5(2):e9166). Effects on inflammation have been widely reported in schizophrenia and appear to involve a mixture of pro- and anti-inflammatory responses, as we have found here (for review, see Miller B. J. et al. (2011) *Biol. Psychiatry.* 70(7):663-71). Previous studies have also reported changes in hormones and growth factors such as chromogranin A, leptin and pancreatic polypeptide (Takayanagi Y. et al. (2013) *Neurosci. Res.* 77(1-2):97-101). Other analytes in the panel are involved in lipid transport and the clotting cascade, consistent with the findings of other studies (Schwarz E. et al. (2012) *Mol. Psychiatry.* 17(5):494-502; Li Y. et al. (2012) *Mol. Biosyst.* 8(10):2664-71). Beyond the prognostic and diagnostic potential, the present findings may lead to applications for personalized medicine approaches. For example, patients exhibiting changes in inflammation pathways may benefit from anti-inflammatory medication as an adjunctive treatment with standard antipsychotics (Muller N. et al. (2013) *Prog. Neuropsychopharmacol. Biol. Psychiatry* 42:146-53).

The debates surrounding the prodromal syndrome arise from the lack of diagnostic tests to predict the 20-30% of individuals who later develop schizophrenia. This raises ethical issues regarding stigmatisation and inappropriate treatment. The current biomarker panel yielded good to excellent performance for prediction of conversion to schizophrenia or psychosis, providing an important step towards development of a diagnostic test for clinical use. However, all clinical tests have a chance of false diagnosis, which should be considered in the context of the clinical application. In testing the prodromal/help-seeker cohort, it was found that incorporation of CAARMS positive subscale scores into the model improved test performance (AUC=0.90) and using CAARMS scores alone yielded lower performance (AUC=0.72). This suggests that a molecular biomarker test used in conjunction with currently used structured interviews may aid in earlier and more accurate diagnosis of schizophrenia than could be achieved with either test alone.

Interpretation

The identification of serum biomarkers for the diagnosis of schizophrenia patients has been previous published (Schwarz E. et al. (2012) *Mol. Psychiatry.* 17(5):494-502; Domenici E. et al. (2010) *PLoS One* 5(2):e9166). In the present study, these findings were extended by performing a meta-analysis of five cohorts (127 patients and 204 controls), considering the joint effect of analytes and validating the biomarker panel in two further independent cohorts (97 patients and 88 controls). Importantly, it was then demonstrated that the panel had good to excellent performance in predicting help-seekers who later converted from prodromal syndrome to schizophrenia, as well as predicting conversion of individuals who did not display overt psychopathology at the time of sample collection. It is not proposed that this test should be used to screen the general population, but the data suggests that application of this test in conjunction with currently used structured interviews may aid early diagnosis of schizophrenia and thereby facilitate early intervention and improved clinical outcomes.

Market analysis has shown that psychiatrists would value a blood test that could help in the prediction of conversion in prodromal individuals, and aid differential diagnostic evaluation (e.g. differentiation between schizophrenia and affective psychosis) (Bahn S. et al. (2011) *Biom. Neuro. Psych. Dis. USA,* 299-327). Ultimately, further developments of the biomarker panel described here could form the basis of a low-cost blood test. It is therefore suggested that the use of such a test in conjunction with a psychiatric assessment will help to position schizophrenia amongst other biological disorders, such as diabetes and heart disease, ameliorating the stigma and providing hope for better diagnostic and treatment approaches.

The invention claimed is:

1. A method comprising:
   (a) obtaining a test biological sample from an individual with prodromal syndrome; and
   (b) quantifying the amounts of a panel of biomarkers in the test biological sample,
   wherein the panel of biomarkers comprises Macrophage migration inhibitory factor (MIF), Pancreatic polypeptide (PPP), Apolipoprotein H (ApoH), Apolipoprotein A1 (ApoA1), Tenascin C (TNC), Interleukin-1 receptor antagonist (IL 1ra), Receptor for advanced glycosylation end products (RAGE), Interleukin 8 (IL 8), Haptoglobin, von Willebrand factor (VWF), Beta-2 microglobulin (B2M), Immunoglobulin A (IgA), Leptin, Testosterone (Total), Follicle-stimulating hormone (FSH), Thyroid stimulating hormone (TSH), Insulin-like growth factor-binding protein 2 (IGFBP2), AXL receptor tyrosine kinase (AXL), Stem Cell Factor (SCF), Factor VII (FVII) and Angiotensin-converting enzyme (ACE).

2. The method according to claim 1, wherein the quantifying is performed by measuring the concentration of the biomarkers in the sample.

3. The method according to claim 1, wherein the quantifying is performed by one or more methods selected from SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC-MS-based technique.

4. The method according to claim 1, wherein the quantifying is performed using an immunological method.

5. The method according to claim 1, wherein the quantifying is performed using a biosensor or a microanalytical, microengineered, microseparation or immunochromatography system.

6. The method according to claim 1, wherein the test biological sample is whole blood, blood serum, plasma, cerebrospinal fluid, urine, saliva, or other bodily fluid, or breath, condensed breath, or an extract or purification therefrom, or dilution thereof.

7. The method of claim 1, further comprising assessing the individual using the Comprehensive Assessment of At-Risk Mental State (CAARMS).

8. The method of claim 1, wherein the individual is drug-naïve.

9. The method of claim 1, further comprising obtaining a second test biological sample from the individual; and
   quantifying the amounts of the panel of biomarkers in the second test biological sample.

10. A method comprising:
    a) obtaining a test biological sample from an individual with prodromal syndrome; and
    (b) quantifying the amounts of a panel of biomarkers in the test biological sample,
    wherein the panel of biomarkers comprises Macrophage migration inhibitory factor (MIF), Pancreatic polypeptide (PPP), Leptin, Factor VII (FVII), Haptoglobin, Receptor for advanced glycosylation end products (RAGE), Tenascin C (TNC), AXL receptor tyrosine kinase (AXL), Follicle-stimulating hormone (FSH), Insulin-like growth factor-binding protein 2 (IGFBP2), Interleukin-1 receptor antagonist (IL 1ra), Beta-2 microglobulin (B2M), Interleukin 8 (IL 8), Stem Cell Factor (SCF), von Willebrand factor (VWF), Angiotensin-converting enzyme (ACE), Apolipoprotein H (ApoH), Immunoglobulin A (IgA), Apolipoprotein A1 (ApoA1), Testosterone (Total), Thyroid stimulating hormone (TSH) and Alpha-2 Macroglobulin (A2M).

11. The method of claim 10, wherein the quantifying is performed by measuring the concentration of the biomarkers in the sample.

12. The method of claim 10, wherein the quantifying is performed by one or more methods selected from SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC-MS-based technique.

13. The method of claim 10, wherein the quantifying is performed using an immunological method.

14. The method of claim 10, wherein the quantifying is performed using a biosensor or a microanalytical, microengineered, microseparation or immunochromatography system.

15. The method of claim 10, wherein the test biological sample is whole blood, blood serum, plasma, cerebrospinal fluid, urine, saliva, or other bodily fluid, or breath, condensed breath, or an extract or purification therefrom, or dilution thereof.

16. The method of claim 10, further comprising assessing the individual using the Comprehensive Assessment of At-Risk Mental State (CAARMS).

17. The method of claim 10, wherein the individual is drug-naïve.

18. The method of claim 10, further comprising obtaining a second test biological sample from the individual; and
quantifying the amounts of the panel of biomarkers in the second test biological sample.

19. A The method comprising:
a) obtaining a test biological sample from an individual with prodromal syndrome; and
(b) quantifying the amounts of a panel of biomarkers in the test biological sample,
wherein the panel of biomarkers comprises Macrophage migration inhibitory factor (MIF), Pancreatic polypeptide (PPP), Leptin, Factor VII (FVII), Haptoglobin, Receptor for advanced glycosylation end products (RAGE), Tenascin C (TNC), AXL receptor tyrosine kinase (AXL), Follicle-stimulating hormone (FSH), Insulin-like growth factor-binding protein 2 (IGFBP2), Interleukin-1 receptor antagonist (IL 1ra), Beta-2 microglobulin (B2M), Interleukin 8 (IL 8), Stem Cell Factor (SCF), von Willebrand factor (VWF), Angiotensin-converting enzyme (ACE), Apolipoprotein H (ApoH), Immunoglobulin A (IgA), Apolipoprotein A1 (ApoA1), Testosterone (Total), Thyroid stimulating hormone (TSH), Carcinoembryonic antigen (CEA), Serum glutamic oxaloacetic transaminase (SGOT) and Interleukin-13 (IL 13).

20. The method of claim 19, wherein the quantifying is performed by measuring the concentration of the biomarkers in the sample.

21. The method of claim 19, wherein the quantifying is performed by one or more methods selected from SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC-MS-based technique.

22. The method of claim 19, wherein the quantifying is performed using an immunological method.

23. The method of claim 19, wherein the quantifying is performed using a biosensor or a microanalytical, microengineered, microseparation or immunochromatography system.

24. The method of claim 19, wherein the test biological sample is whole blood, blood serum, plasma, cerebrospinal fluid, urine, saliva, or other bodily fluid, or breath, condensed breath, or an extract or purification therefrom, or dilution thereof.

25. The method of claim 19, further comprising assessing the individual using the Comprehensive Assessment of At-Risk Mental State (CAARMS).

26. The method of claim 19, wherein the individual is drug-naïve.

27. The method of claim 19, further comprising obtaining a second test biological sample from the individual; and
quantifying the amounts of the panel of biomarkers in the second test biological sample.

* * * * *

UNITED STATES PATENT AND TRADEMARK OFFICE
CERTIFICATE OF CORRECTION

PATENT NO. : 10,197,580 B2
APPLICATION NO. : 15/125069
DATED : February 5, 2019
INVENTOR(S) : Sabine Bahn et al.

Page 1 of 1

It is certified that error appears in the above-identified patent and that said Letters Patent is hereby corrected as shown below:

In the Claims

Column 39, Line 15, Claim 19, please delete "The"

Signed and Sealed this
Fourteenth Day of April, 2020

Andrei Iancu
*Director of the United States Patent and Trademark Office*